United States Patent
Hanypsiak et al.

(10) Patent No.: US 8,360,969 B2
(45) Date of Patent: Jan. 29, 2013

(54) SECURABLE CANNULA AND METHOD

(75) Inventors: Bryan T. Hanypsiak, Shoreham, NY (US); Mark G. Frantz, New York, NY (US); Mark A. Williams, Mentor, OH (US); Joseph P. Frantz, Aurora, OH (US); Charles P. Chesnes, Chardon, OH (US); Paul L. Erickson, Eastlake, OH (US); Stephanie A. S. Harrington, Mentor, OH (US); Jennifer S. Innamorato, Twinsburg, OH (US); Mark S. Goodin, Solon, OH (US)

(73) Assignee: Frantz Medical Development, Ltd., Mentor, OH (US)

( * ) Notice: Subject to any disclaimer, the term of this patent is extended or adjusted under 35 U.S.C. 154(b) by 695 days.

(21) Appl. No.: 12/057,784

(22) Filed: Mar. 28, 2008

(65) Prior Publication Data
US 2008/0242930 A1 Oct. 2, 2008

Related U.S. Application Data

(60) Provisional application No. 60/908,777, filed on Mar. 29, 2007.

(51) Int. Cl.
*A61B 1/313* (2006.01)
*A61B 17/34* (2006.01)
(52) U.S. Cl. ..................................... 600/184; 606/185
(58) Field of Classification Search .................. 600/184; 604/103.03, 104–109; 128/852; 606/108, 606/185, 190, 200
See application file for complete search history.

(56) References Cited

U.S. PATENT DOCUMENTS

| | | | |
|---|---|---|---|
| 540,835 A * | 6/1895 | Gunning | 604/106 |
| 3,039,468 A * | 6/1962 | Price | 604/540 |
| 4,608,965 A | 9/1986 | Anspach, Jr. et al. | |
| 4,673,393 A | 6/1987 | Suzuki et al. | |
| 5,197,971 A | 3/1993 | Bonutti | |
| 5,203,773 A | 4/1993 | Green | |
| 5,263,937 A | 11/1993 | Shipp | |
| 5,279,564 A | 1/1994 | Taylor | |
| 5,279,575 A | 1/1994 | Sugarbaker | |
| 5,309,894 A | 5/1994 | Heckele et al. | |
| 5,330,501 A | 7/1994 | Tovey et al. | |
| 5,385,552 A | 1/1995 | Haber et al. | |

(Continued)

FOREIGN PATENT DOCUMENTS

| | | |
|---|---|---|
| EP | 0 526 721 | 2/1993 |
| WO | 96/23536 | 8/1996 |

(Continued)

OTHER PUBLICATIONS

International Search Report and Written Opinion of the International Searching Authority of corresponding International Application No. PCT/US2008/058613, filed Mar. 28, 2008.

*Primary Examiner* — Ryan Severson
(74) *Attorney, Agent, or Firm* — Tarolli, Sundheim, Covell & Tummino LLP

(57) ABSTRACT

A medical device suitable for introducing a medical instrument into a patient includes an outer cannula and at least one arm connected to the cannula toward a proximal portion of the at least one arm. The at least one arm is deployable between a closed position and an open position. An inner member is telescopically received in the outer cannula to hold each arm in the closed position. The inner member is deployable to disengage from the arm after the device is inserted into a patient, thereby freeing the arm to be deployed to the open position where it helps hold the outer cannula in the patient. The inner member includes an inner cannula and/or a trocar.

30 Claims, 35 Drawing Sheets

U.S. PATENT DOCUMENTS

| | | | |
|---|---|---|---|
| 5,549,595 A | 8/1996 | Freitas | |
| 5,779,697 A | 7/1998 | Glowa et al. | |
| 5,817,062 A * | 10/1998 | Flom et al. | 604/174 |
| 5,857,999 A | 1/1999 | Quick et al. | |
| 5,928,260 A * | 7/1999 | Chin et al. | 606/200 |
| 5,971,960 A | 10/1999 | Flom et al. | |
| 6,228,063 B1 | 5/2001 | Aboul-Hosn | |
| 6,436,119 B1 | 8/2002 | Erb et al. | |
| 6,500,170 B2 | 12/2002 | Palmer et al. | |
| 6,599,304 B1 | 7/2003 | Selmon et al. | |
| 6,808,492 B2 | 10/2004 | Snyder | |
| 2003/0023201 A1 | 1/2003 | Aboul-Hosn et al. | |
| 2007/0162066 A1 | 7/2007 | Lyon | |
| 2008/0086165 A1 | 4/2008 | Lyon et al. | |

FOREIGN PATENT DOCUMENTS

WO     2005/037079     4/2005

\* cited by examiner

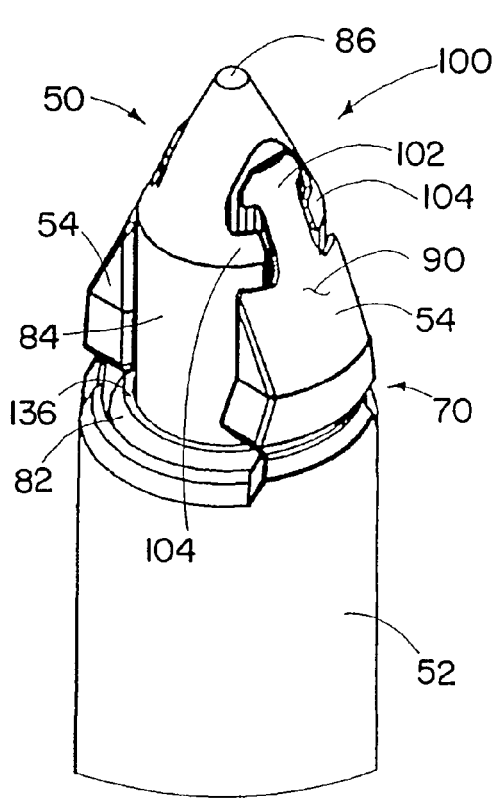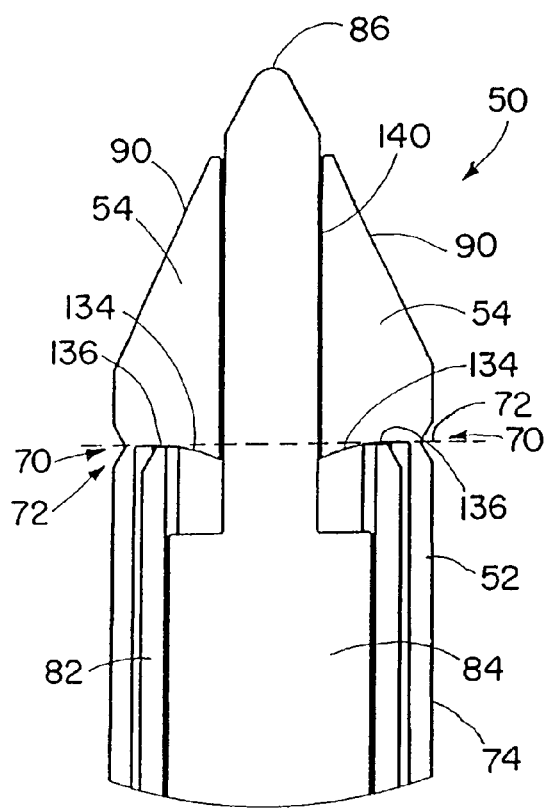
FIG. 4    FIG. 5
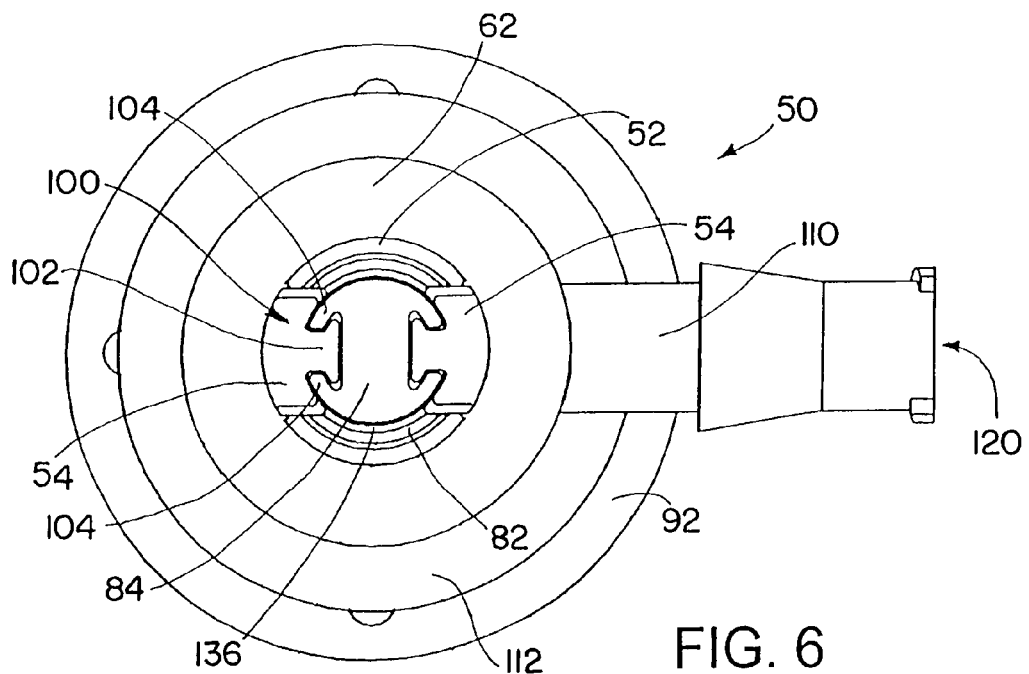
FIG. 6

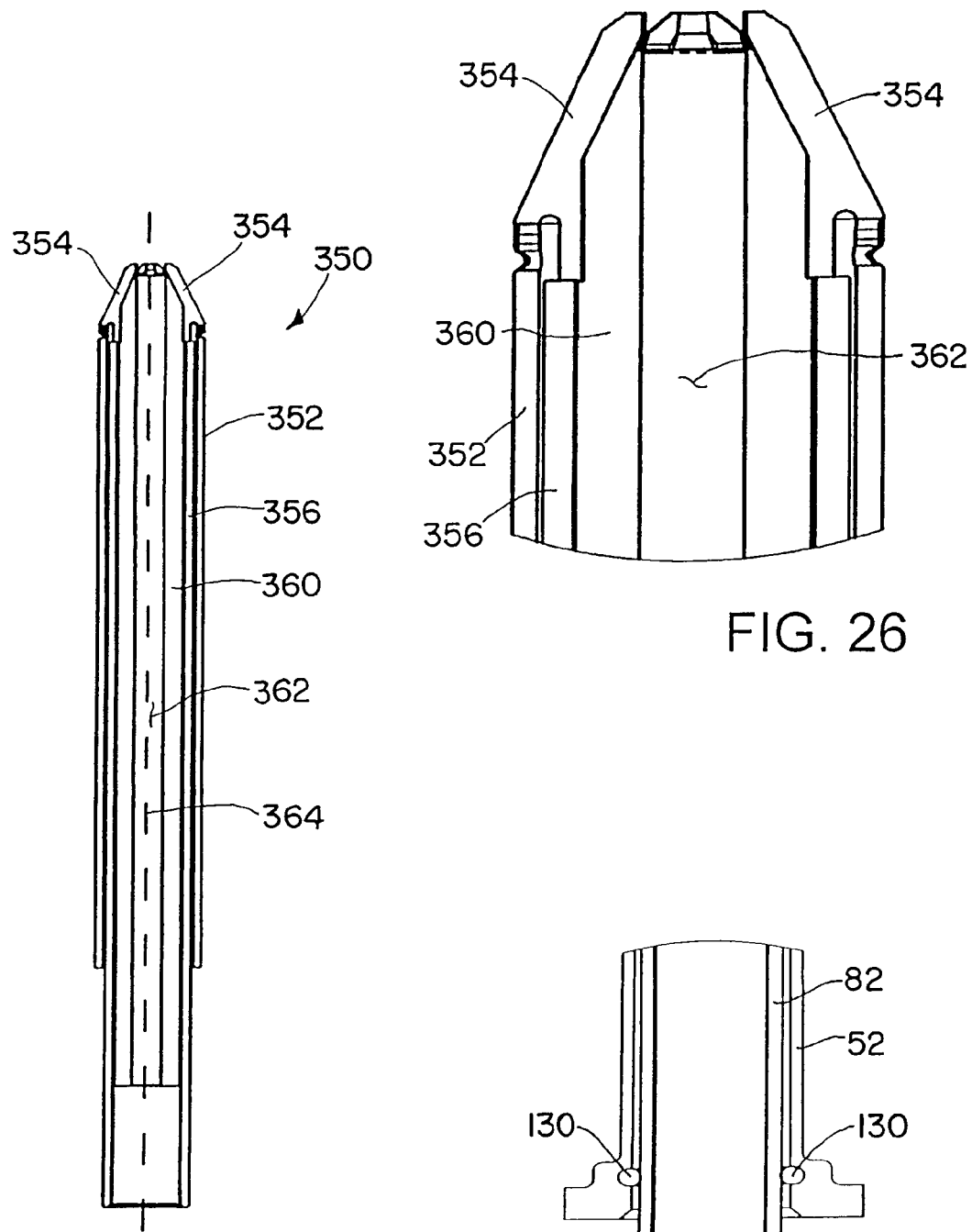
FIG. 26
FIG. 25
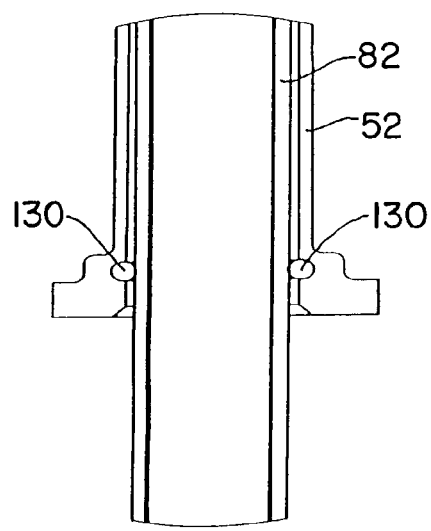
FIG. 24

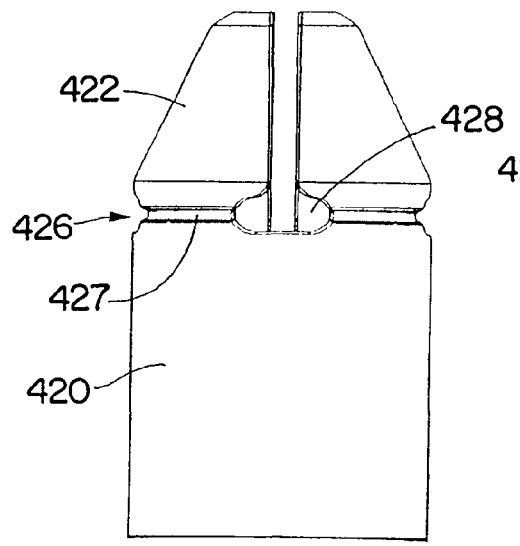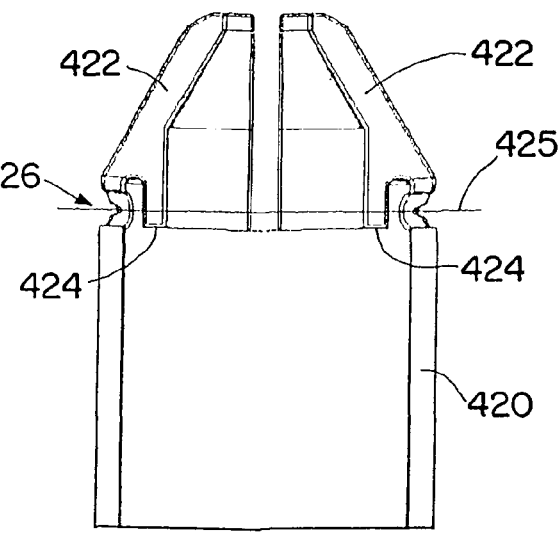
FIG. 31     FIG. 32
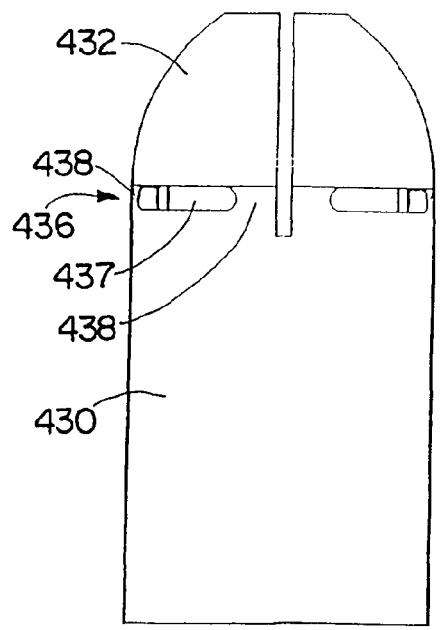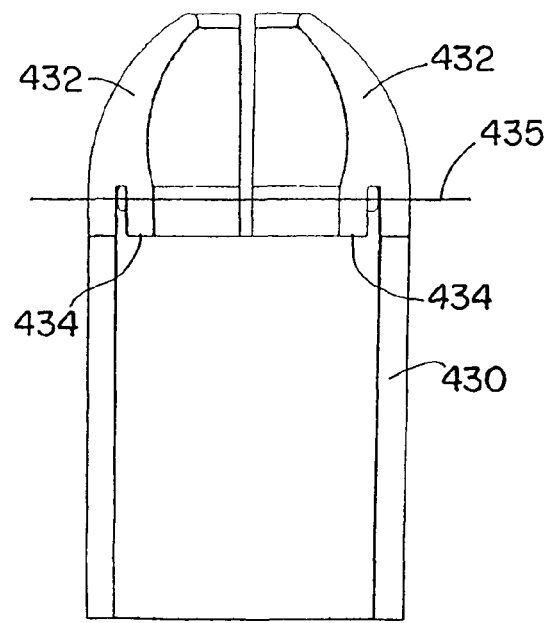
FIG. 33     FIG. 34

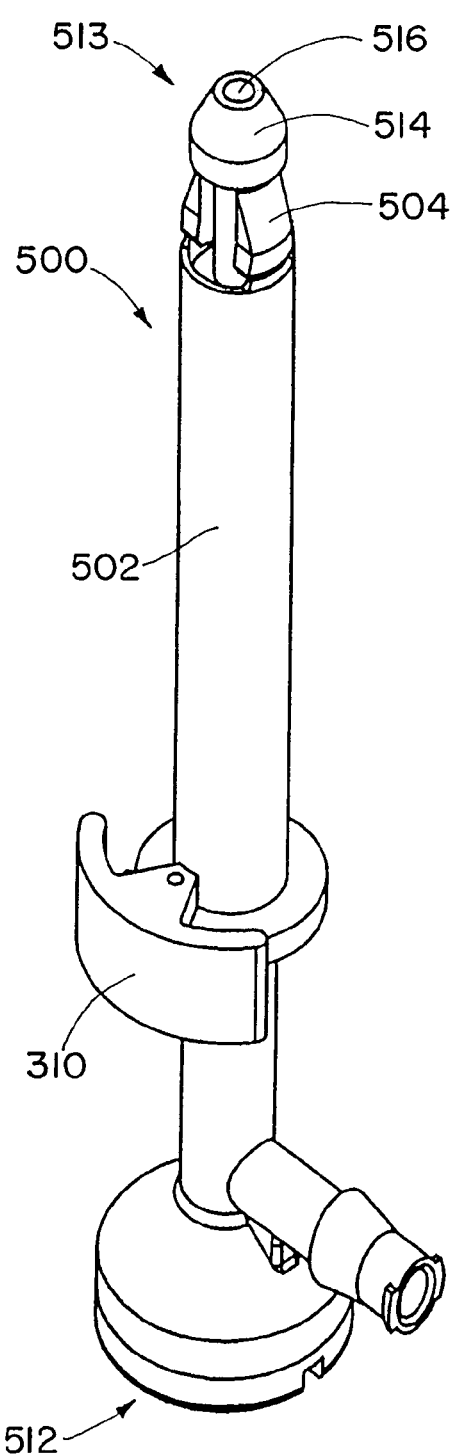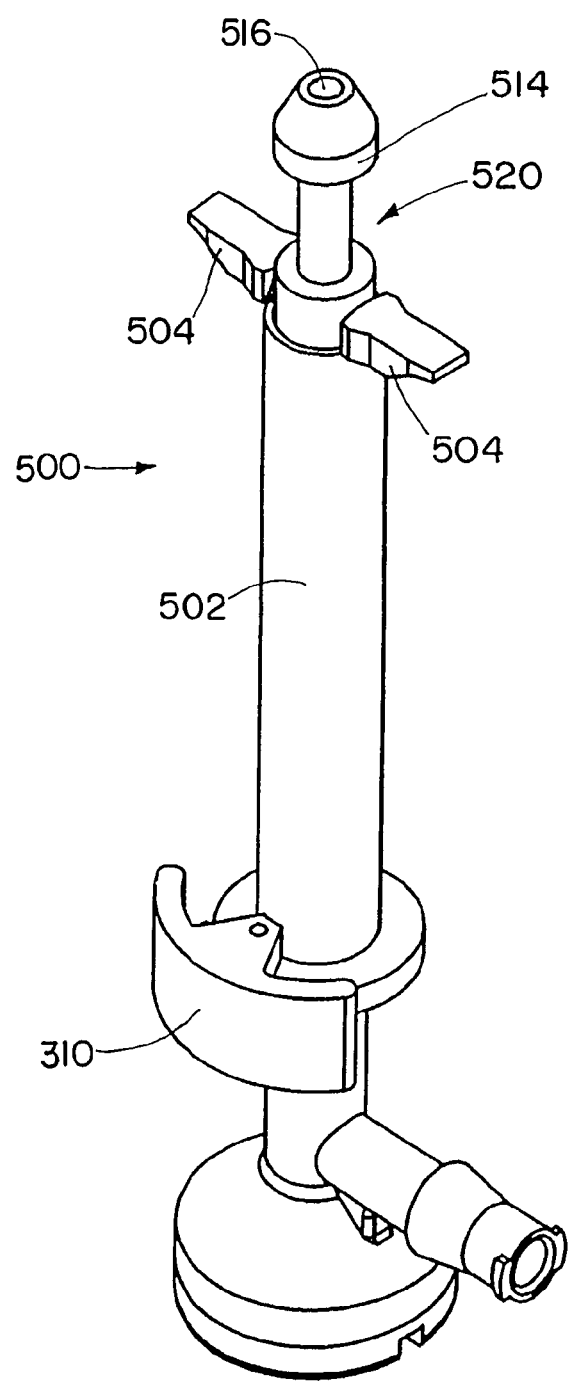
FIG. 35
FIG. 36

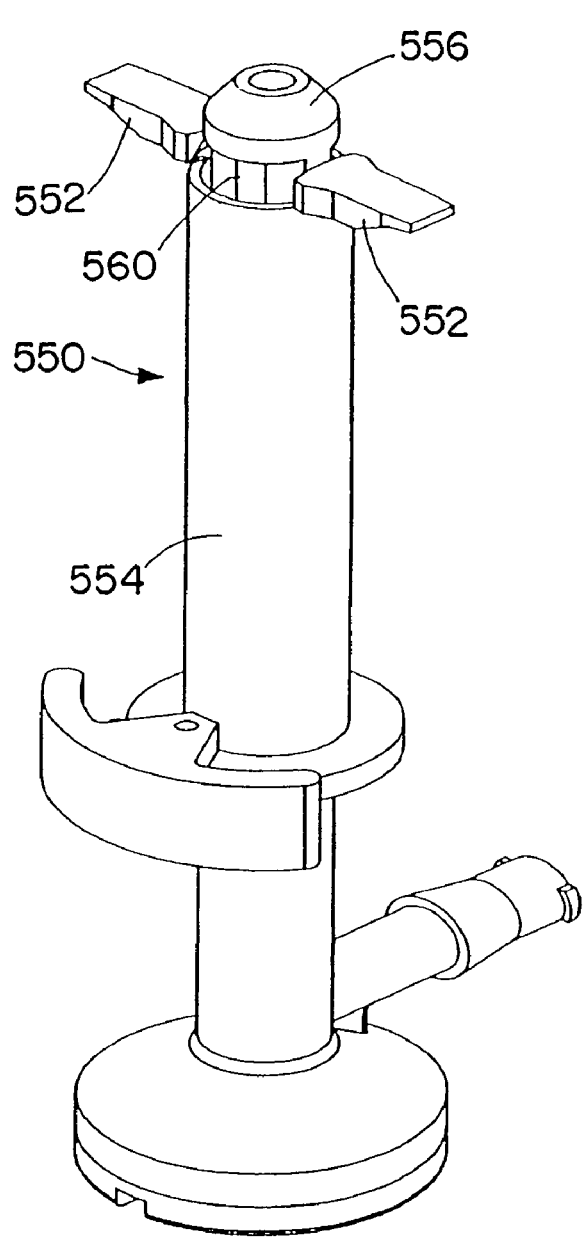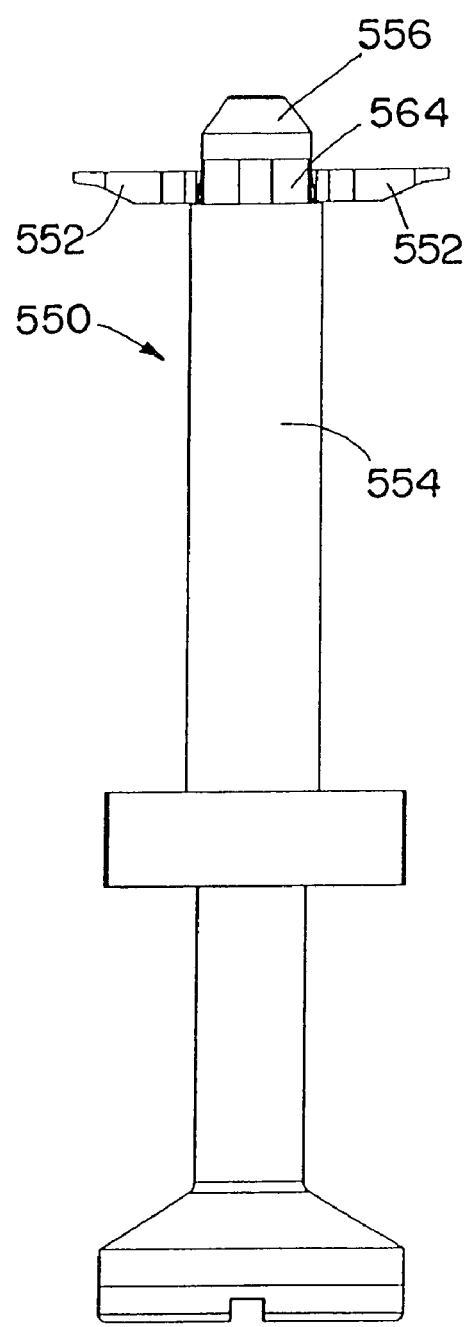
FIG. 48
FIG. 49

SECURABLE CANNULA AND METHOD

This application claims the benefit of U.S. Provisional Patent Application No. 60/908,777, filed Mar. 29, 2007, which is hereby incorporated herein in its entirety.

FIELD OF THE INVENTION

The present invention relates to a cannula for endoscopic surgery and a method for its use.

BACKGROUND

In endoscopic surgery, a cannula is used to maintain an open passage into a body cavity for introducing surgical instruments into a surgical site. Typically, the body cavity is pressurized with a fluid (such as sterile liquids or gases), which also can be provided via the cannula, to expand the cavity, facilitate maneuverability of the surgical instruments, and to maintain a clear field of view for the surgeon. Soft tissue adjacent the cavity may swell as the tissue absorbs fluid. The cannula also maintains the passage to facilitate surgical instrument insertion and removal.

One problem that has existed with prior cannulas is that they may be partially or completely dislodged from the patient as the instruments are manipulated or exchanged via the cannula, particularly during instability surgery involving loose or thin capsular tissue. If the cannula is partially or completely pulled out of the patient, the body cavity may collapse or fill with fluid or blood, the surgeon loses sight of and access to the cavity, and the surgical procedure is interrupted while the portal into the body cavity is reestablished. During this time, for cavity distention with sterile liquids, the soft tissue can continue to absorb fluid and soften, making it difficult to reinsert the cannula and leading to an increased risk of surgical complications. While different techniques have been employed to improve cannulas and their ability to remain in place during surgery, we believe that further improvements are warranted.

SUMMARY

The present invention improves on prior cannula systems for endoscopic surgery, including arthroscopic and laparoscopic surgery, for example. The present invention thus provides a cannula system and method for easily assembling and inserting a cannula into a patient's body, and actuating a mechanism to hold the cannula in place during the procedure. The cannula is easily removed at the end of the surgical procedure.

In particular, the present invention provides a medical device in the form of a cannula system that includes an outer cannula, at least one arm that is deployable between a closed position and an open position and is connected to the outer cannula toward a proximal end of the at least one arm. The cannula system also includes an inner member telescopically received in the outer cannula that engages at least one arm and holds it in the closed position. The inner member is deployable to disengage the inner member from the at least one arm. The inner member may include a trocar telescopically received within the outer cannula, or an inner cannula telescopically received in the outer cannula, or both, with the trocar telescopically received within the inner cannula.

In general, when in the closed position one or more arms are aligned relatively closer to a longitudinal axis of the cannula, and when in the open position each arm is aligned relatively closer to a plane perpendicular to the longitudinal axis of the cannula.

The present invention also provides a cannula system suitable for introducing a medical instrument into a patient. The system includes (A) an outer cannula having (i) a tubular portion with a longitudinal through hole, and (ii) at least one arm integrally connected to a distal region of the tubular portion. The at least one arm is pivotable between a closed position and an open position rotatably displaced relative to the closed position, and the at least one arm has a cam surface that extends inwardly into an extension of the through hole. The system also includes (B) an inner cannula extending into and telescopically received in the through hole in the outer cannula. The inner cannula has a tubular shape with a longitudinal through hole, and is longitudinally deployable along a path within the through hole in the outer cannula. Finally, the system includes (C) a trocar removably inserted into the inner cannula. Moreover, the at least one arm has an element that corresponds to an element of the trocar, and those elements cooperate to hold the at least one arm in the closed position, whereupon longitudinal deployment of the inner cannula engages the cam, deploys the at least one arm to the open position, and holds the at least one arm in the open position.

The present invention also provides a method of using a cannula system for introducing a medical instrument into a patient. The method includes (A) the step of inserting the cannula system into the body of a patient. The cannula system includes an outer cannula and an inner member telescopically received in the outer cannula. And the outer cannula has at least one arm attached thereto by a connection toward a proximal end of the at least one arm, and the at least one arm is held in a closed position by the inner member. The method also includes (B) the step of deploying the inner member or a part thereof to disengage the at least one arm from the inner member and allow the at least one arm to deploy to an open position displaced from the closed position.

Yet another cannula system provided in accordance with the present invention includes an outer cannula, at least one arm that is deployable between a closed position and an open position, and an inner member telescopically received in the outer cannula. The at least one arm is connected to the outer cannula, and the inner member releasably holds the at least one arm in the closed position. Longitudinal movement of the inner member is necessary to release the at least one arm from the closed position, and a locking mechanism secures the inner member in a fixed location relative to a longitudinal axis of the outer cannula to prevent the longitudinal movement of the inner member. This helps to hold the at least one arm in the closed position during insertion and prevent the at least one arm from accidentally moving from the closed position.

The present invention also provides a cannula system that includes an outer cannula, at least one arm that is deployable between a closed position and an open position and is connected to the outer cannula, an inner cannula telescopically received in the outer cannula, and a catch mechanism that releasably limits longitudinal travel of the inner cannula relative to the outer cannula when the at least one arm is in the open position.

The foregoing and other features of the invention are more fully described and particularly pointed out in the claims. The following description and annexed drawings set forth in detail several illustrative embodiments, these embodiments being indicative of but a few of the various ways in which the principles of the invention may be employed.

BRIEF DESCRIPTION OF THE DRAWINGS

FIG. 4 is an enlarged perspective view of a distal region of the cannula system of FIG. 1.

FIG. 5 is an enlarged view of a distal region of the cross-sectional view of FIG. 3.

FIG. 6 is a top view of the cannula system of FIG. 1.

FIG. 24 is a partial elevational cross-sectional view of the cannula system of FIG. 3.

FIG. 25 is an elevational cross-sectional view of another embodiment of a cannula system provided by the present invention.

FIG. 26 is an enlarged view of a distal region of the cannula system of FIG. 25.

FIG. 31 is an elevational view of a distal region of an outer cannula provided by the present invention.

FIG. 32 is an elevational cross-sectional view of the outer cannula of FIG. 31.

FIG. 33 is an elevational view of a distal region of an outer cannula provided by the present invention.

FIG. 34 is an elevational cross-sectional view of the outer cannula of FIG. 33.

FIG. 35 is a perspective view of yet another embodiment of cannula system provided is accordance with the present invention is a closed position.

FIG. 36 is a perspective of the cannula system of FIG. 35 in an open position.

FIG. 48 is a perspective of the cannula system of FIG. 45 with the inner member rotated and proximally retracted from the distally extended position shown in FIG. 45.

FIG. 49 is a side view of the cannula system of FIG. 48.

DETAILED DESCRIPTION

Figures 1, 2:
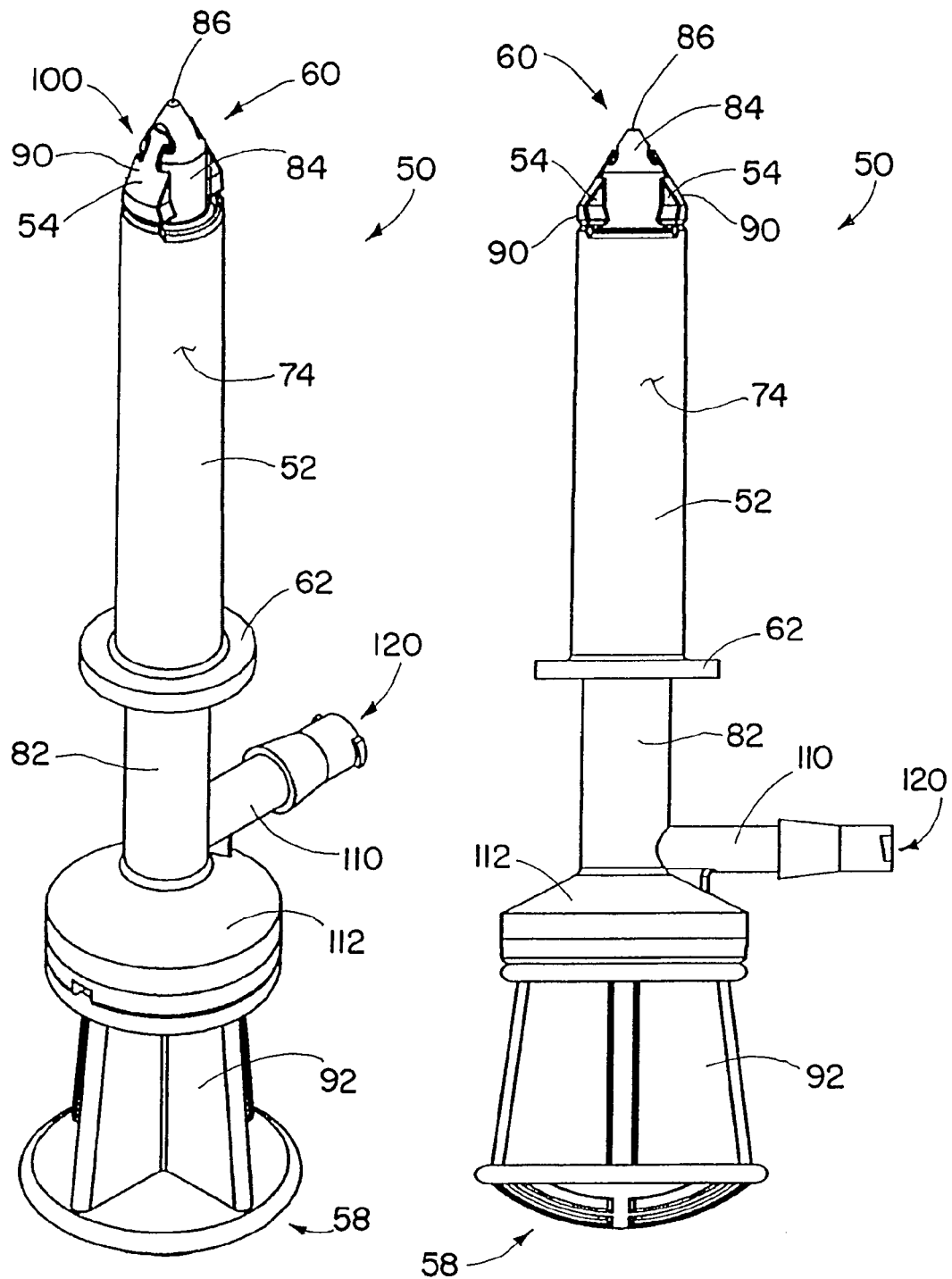
FIG. 1 is a perspective view of an exemplary cannula system provided in accordance with the present invention.
FIG. 2 is a side view of the cannula system of FIG. 1.
Figure 3:
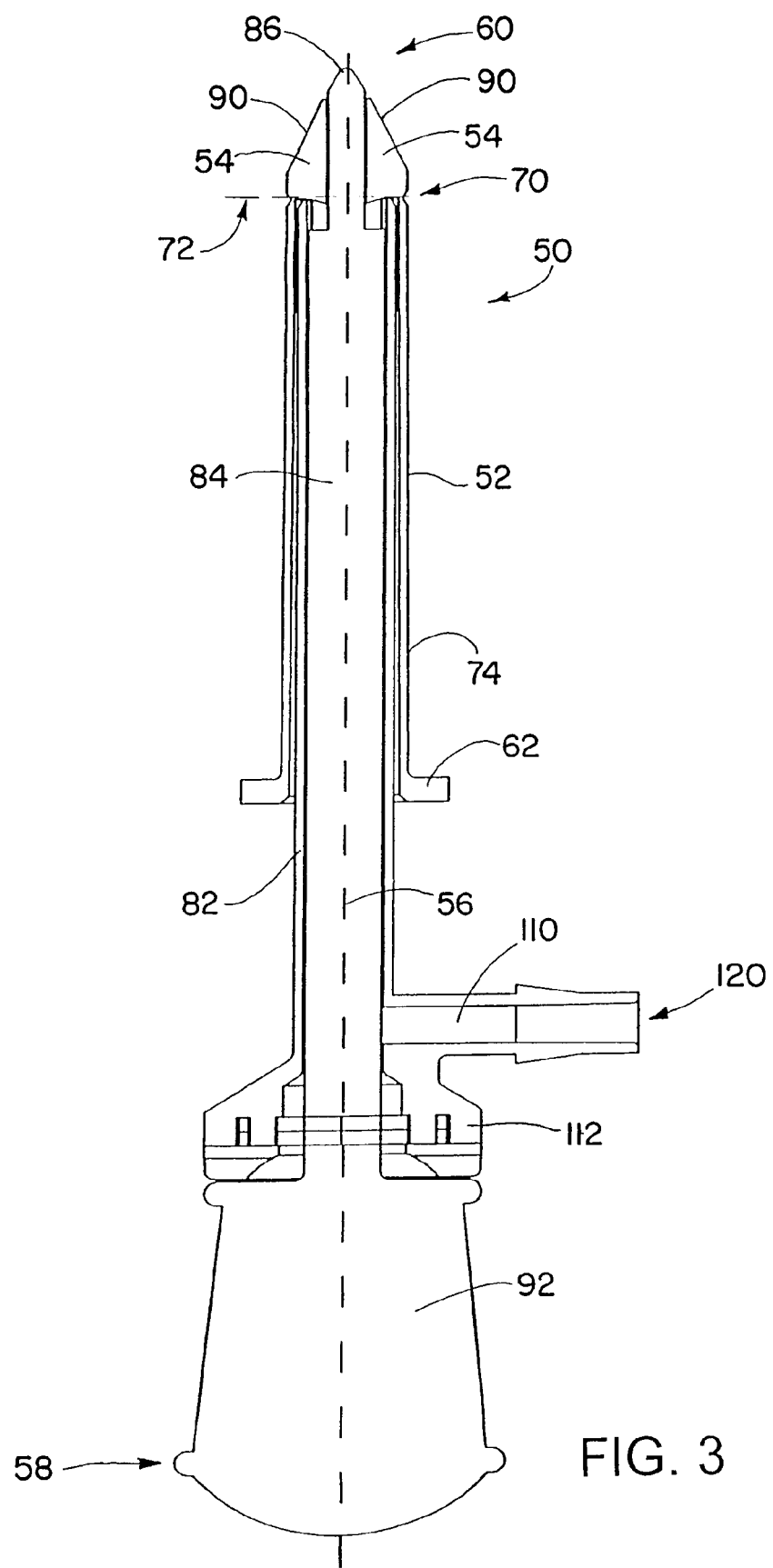
FIG. 3 is a cross-sectional view of the cannula system of FIG. 2.
Figures 7, 8:
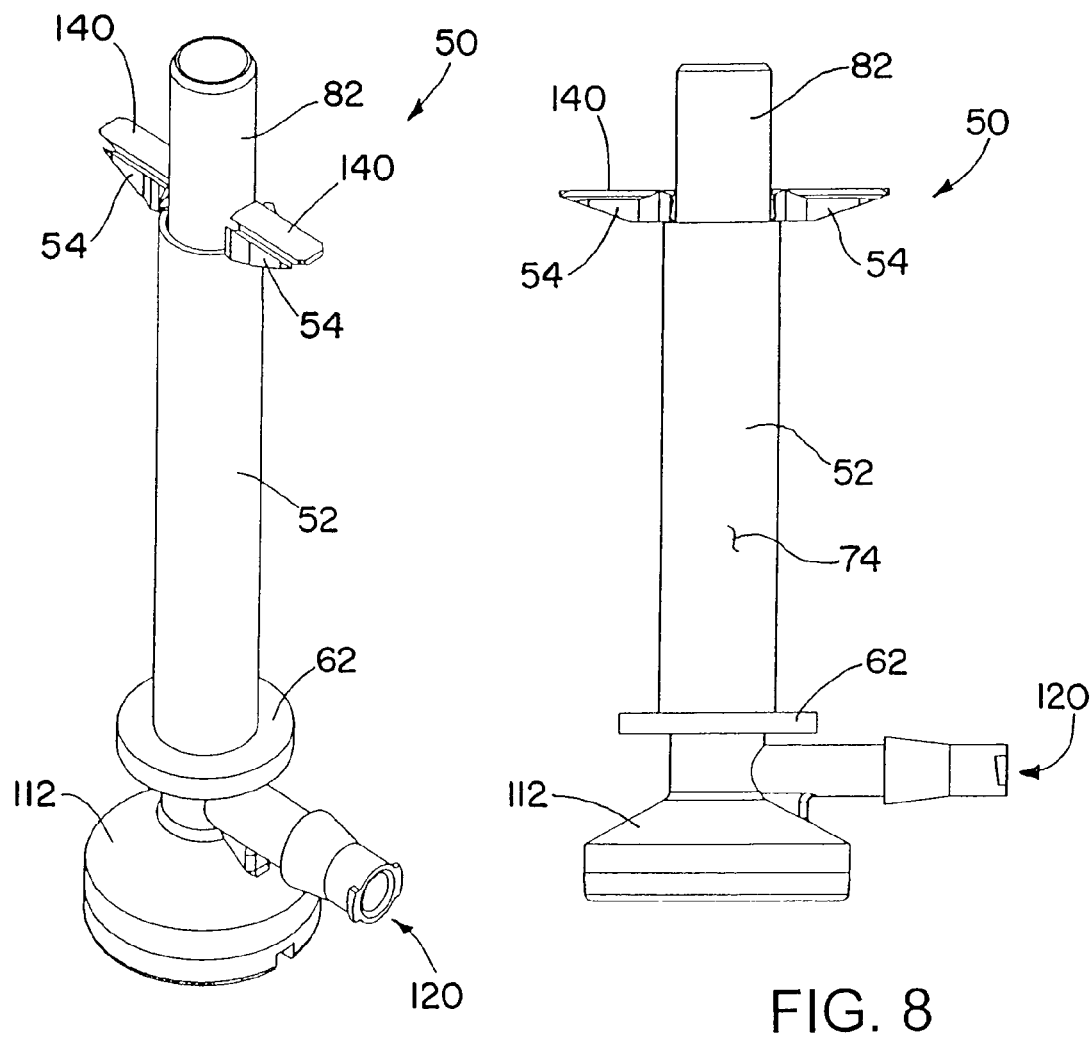
FIG. 7 is a perspective view of the cannula system of FIG. 11 with arms thereof in an open position.
FIG. 8 is a side view of the cannula system of FIG. 7.
Figure 9:
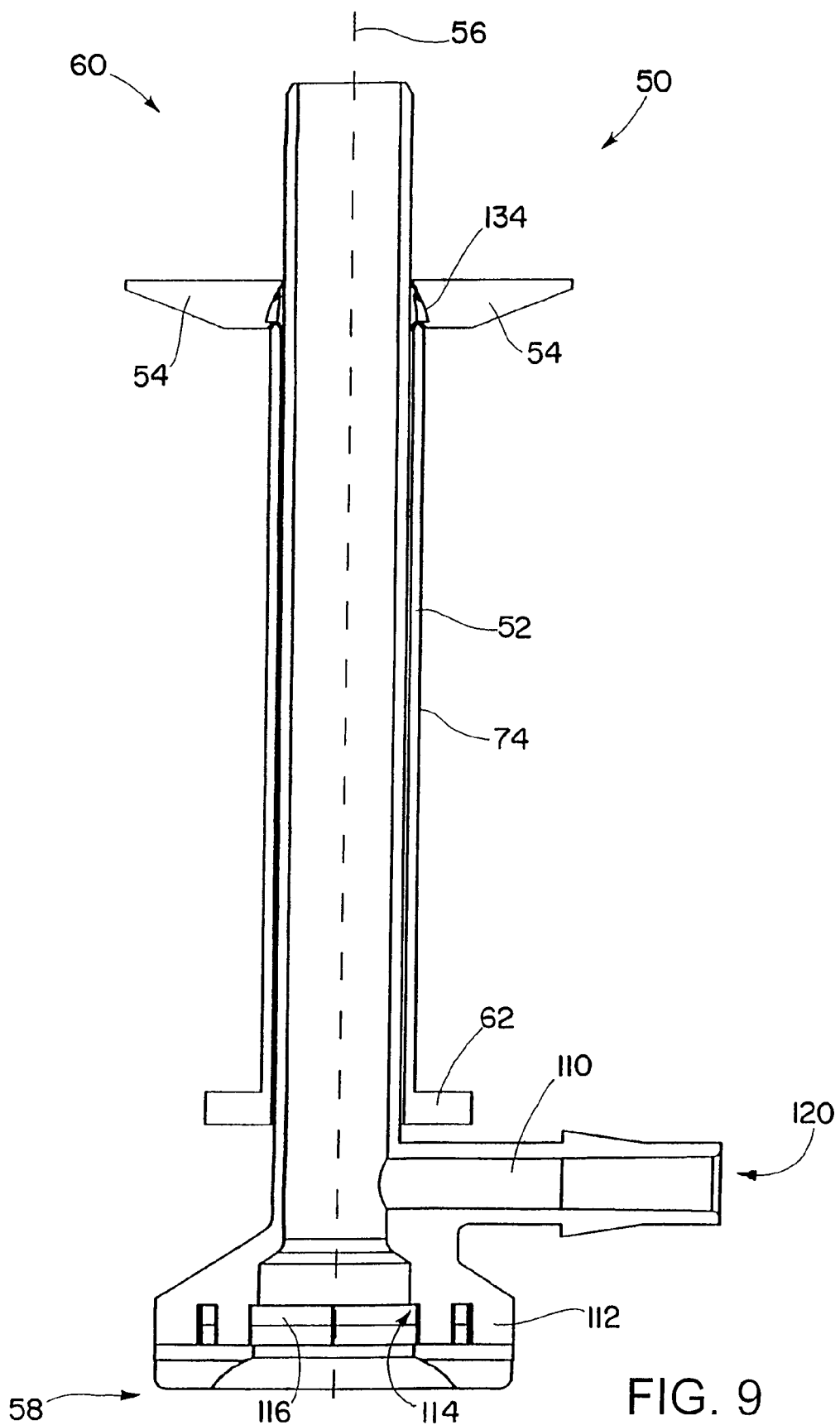
FIG. 9 is a cross-sectional elevational view of the cannula system of FIG. 8.
Figure 10:
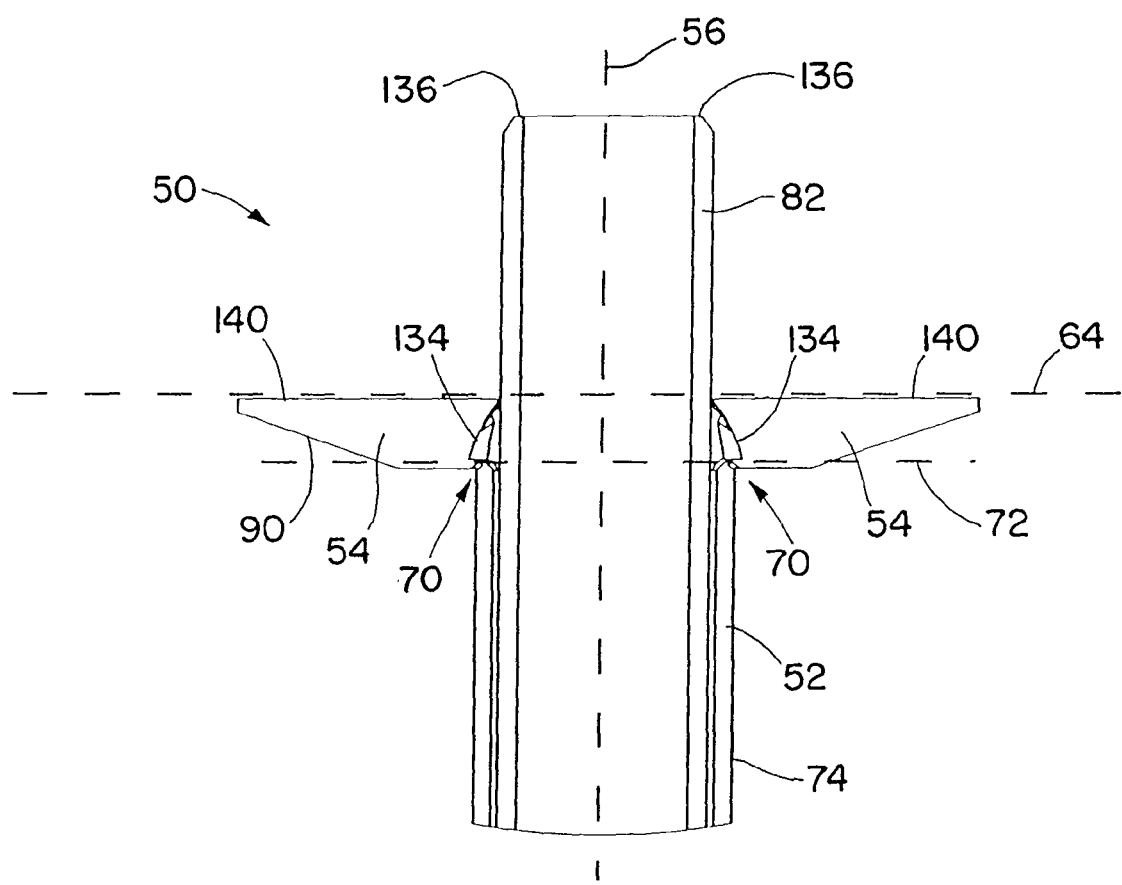
FIG. 10 is an enlarged view of a distal region of the cross-sectional view of FIG. 9.

Referring now to the drawings in detail and initially to FIGS. 1-10, the present invention provides a medical device 50 suitable for introducing a medical instrument into a patient during endoscopic surgery. Endoscopic surgery includes arthroscopic and laparoscopic surgery, for example. More particularly, the invention provides a medical device for endoscopic surgery and a related method for inserting a cannula into a patient and using one or more deployable wings or arms to hold the cannula in the patient's body during surgery. Consequently the device 50 alternatively may be referred to as a cannula system 50.

The cannula system 50 has a longitudinal axis 56. Spaced along the longitudinal axis 56, the cannula system 50 has a proximal end 58 and a distal end 60 opposite the proximal end 58. Likewise, the distal direction passes substantially parallel to the longitudinal axis 56 through the proximal end 58 toward the distal end 60, and the proximal direction is opposite the distal direction. The distal end 60 is the end that is inserted into the patient's body, and different portions of the cannula system 50 and its components will be described with respect to corresponding proximal and distal ends and relative positions and directions with respect to the proximal and distal ends.

An exemplary cannula system 50 provided in accordance with the invention includes a cannula 52 with at least one arm 54 connected to the cannula 52. The at least one arm 54 is deployable between a closed position (FIGS. 1-6) and an open position (FIGS. 7-10) displaced from the closed position, and any position in between. Deployed means intentionally arranged or moved or caused to move. Deployed also is not limited to any particular direction or arrangement. The system 50 further includes an inner member telescopically received in the cannula 52. Consequently, the cannula 52 is also referred to as an outer cannula. The inner member includes one or more elements that engage at least one arm 54 to hold the one or more arms 54 in the closed position.

A cannula is a tube, and the cannula 52 typically is a cylindrical tube with a circular cross-section and a longitudinal axis aligned with the longitudinal axis 56 of the system 50. The outer surface of the cannula 52 generally is relatively smooth to minimize abrasion or other tissue damage. Alternatively, the outer surface can include ribs or threads to help hold the cannula 52 in the surgical site. The illustrated cannula 52 also includes an outwardly-extending flange 62 near a proximal end that facilitates manipulating the cannula 52.

The cannula 52 generally includes at least one arm, and typically includes two to four circumferentially-spaced arms, pivotably connected to a distal region of the cannula 52. The embodiment shown in FIG. 1 includes a pair of opposed arms 54. Using just two arms facilitates the use of multiple cannula systems in closer proximity than would be possible if the cannula system had more arms. The arms are connected to the outer cannula 52 via a pivot located in a proximal portion of each arm 54, the arms extending in a distal direction from the pivot when the arms are in a closed position. As shown in FIG. 1, in the closed position the arms 54 are aligned relatively closer to the longitudinal axis 56 of the cannula 52, and in the open position the arms 54 are aligned relatively closer to a plane 64 (FIG. 10) perpendicular to the longitudinal axis 56. The arms 54 can be deployed to a position between the open and closed positions to allow manipulation of the device 50 in the surgical site, and then be deployed to the open position to secure the cannula system 50 in position relative to the body.

As the arm or arms 54 move to the open position, they can act as retractors, pulling back soft tissue in the area and clearing a space in the body cavity as the arm or arms sweep through an area distally located relative to the pivot point at a proximal end of each arm. Multiple cannulas may be employed as needed. Particularly for designs with fewer arms, multiple cannula systems can be used in close proximity without the arms of the various cannula systems interfering with each other.

In the illustrated embodiment each arm 54 is integrally connected to the distal region of the cannula 52 with a living hinge 70. In this example each arm 54 is pivotable about a point generally in a plane 72 that is substantially perpendicular to the longitudinal axis of the cannula 52. The pivot point generally also lies within a hypothetical cylinder having infinite length and a diameter defined by an outer surface 74 of the outer cannula 52. The outer cannula 52 and the arms 54 typically are made of a plastic, which generally has some degree of flexibility and may impart some spring characteristics to the living hinge 70. Other materials also may be suitable. The living hinge 70 may be formed by a reduced material thickness at the pivot point in the form of a recess, slot, slit, hole or other reduction in the amount of material. Additionally, as may be seen in a comparison of the various embodiments disclosed herein, the living hinge may be formed from a single connection or multiple circumferentially-spaced connections with variations in wall thickness and/or one or more holes or slots in between.

The inner member is deployable to disengage the inner member from the arm or arms 54 to allow the arm or arms 54 to deploy toward the open position. The inner member includes a trocar, another cannula, which can be referred to as an inner cannula, or both, telescopically received in the aforementioned cannula 52, which accordingly can be referred to as an outer cannula. In the embodiment shown in FIG. 1, an inner cannula 82 is telescopically received within the outer cannula 52, and a trocar 84 is telescopically received within the inner cannula 82.

The trocar 84 generally has a pointed distal end or tip 86 that facilitates guiding the cannula system 50 through the body to the surgical cavity. The tip 86 may have a cone shape with a rounded and smaller diameter distal end, such as that shown in the illustrated embodiment. The arm or arms 54 typically have an exterior surface 90 that further extends the taper in diameter from the trocar 84 to the exterior diameter of the outer cannula 52 when held in the closed position. The trocar 84 also has a handle portion 92 in a proximal region that is larger than the through hole in the inner cannula 82. This enlarged handle portion 92 thus limits the distance the trocar 84 can advance in the inner cannula 82. A proximal end of the handle portion 92 may have a rounded contour, as in the illustrated embodiment, to fit comfortably in the palm of a hand and provide a bearing surface for pushing the cannula system 50 into the body.

The element or elements that hold the one or more arms 54 in the closed position can include a groove, and that groove can form part of a dovetail joint 100, as shown in the illustrated embodiment. In the dovetail joint 100, one or more tails 102 protrude from one of either an arm 54 or the inner member, in this case the trocar 84. At least two spaced-apart pins 104 extend along at least part of the length of the other of either the arm 54 or the inner member, such as the trocar 84, to form the groove or slot for the dovetail tail 102 to extend into. As is typical of a dovetail joint 100, the tail 102 can have a variety of shapes but is wider at its outer end than at its base, and it mates with a groove defined by the pins 104 that has a corresponding shape. The corresponding parts of the dovetail joint 100 are only movable relative to each other in a direction parallel to the longitudinal axis 56 of the cannula system 50, thereby preventing the tail 102 from being withdrawn from the groove in any direction other than in that longitudinal direction. The dovetail joint 100 thus allows the trocar 84 or other inner member to deploy and withdraw longitudinally, in a direction parallel to the longitudinal axis 52 of the cannula, but prevents the arm or arms 54 from pivoting away from the closed position until released from the dovetail joint.

Although in the illustrated cannula system 50 each arm 54 engages the trocar 84, alternatively the arms may interconnect with each other, with only one arm engaging the trocar 84 or other inner member. Put another way, the cannula system may include a plurality of arms, at least one first arm having a first element that engages the inner member, and at least one second arm having a second element that engages the first arm when at least one first arm is in the closed position. To hold all the arms in the closed position, at least one arm overlaps and/or interlocks with at least one other arm. Just such a system is shown in FIGS. 51-55, described below.

In the illustrated embodiment, removing the trocar 84 is a simple matter of pulling it out of the inner cannula 82 along the longitudinal axis 56. Once the trocar 84 is removed, the inner cannula 82 can be advanced to deploy the arms 54 to the open position and surgical instruments and fluids can be introduced through the inner cannula 82 to the surgical site.

Figure 23:
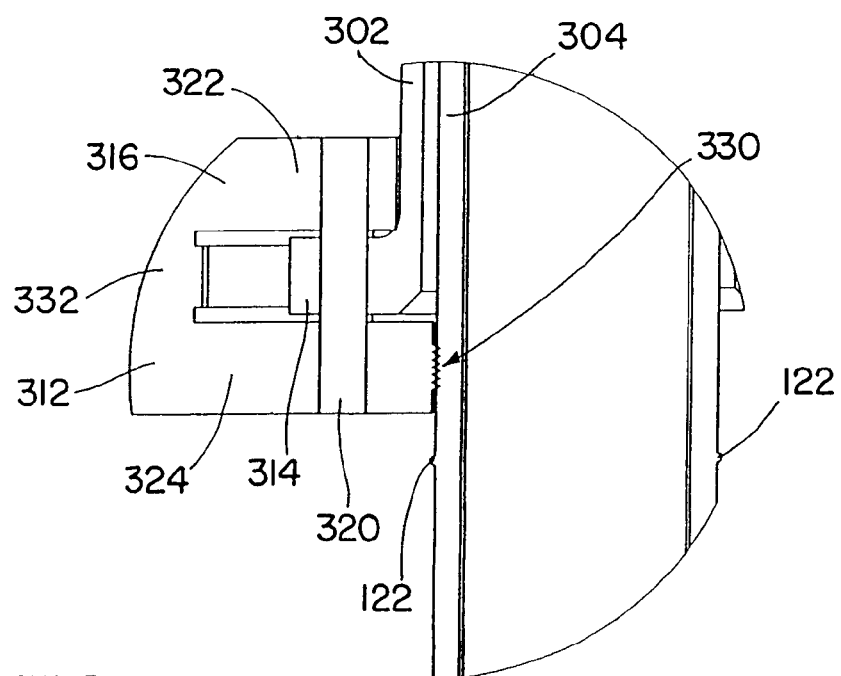
FIG. 23 is an elevational cross-sectional view of FIG. 19.

The inner cannula 82 generally is longer than the outer cannula 52 and thus may protrude from the outer cannula 52. In a proximal region of the inner cannula 82, the inner cannula 82 includes a transverse passage 110 for the insertion and removal of fluid. The transverse passage 110 also provides a sampling port 120 and may include a Luer lock to supply or withdraw fluids from the surgical site. The sampling port 120 also facilitates providing a variable flow rate into and out of the surgical site. Finally, the transverse passage 110 may provide a positive stop for the maximum distal extension or advancement of the inner cannula 82 relative to the outer cannula 52. Alternatively, the inner cannula 82 may include a protrusion 122 (FIG. 23) extending from its outer surface that limits the advancement of the inner cannula relative to the outer cannula 52. A protrusion also may provide additional resistance in withdrawing the inner cannula, acting as an indicator for deployment of the one or more arms 54. The transverse passage 110 may be omitted from some embodiments, however, in which case irrigation and suction may be provided via the longitudinal through hole in the inner cannula 82 or separate from the cannula system 50.

The inner cannula 82 includes an enlarged proximal end portion 112 with a seat 114 for a through-hole seal 116. The through-hole seal 116 substantially seals the through-hole in the inner cannula 82, which helps to maintain the pressure of the fluid while providing access for the surgical instruments along the longitudinal axis 56 of the inner cannula 82 and the outer cannula 52. An exemplary through-hole seal 116 includes one or more slits in each of at least two different layers of material, where the slits in each layer pass through the longitudinal axis 56 of the cannula but otherwise generally are not aligned. An exemplary through-hole seal 116 is made of silicon, which tends to enhance the maneuverability of the inserted instrument within the inner cannula diameter while restricting fluid leakage. The cannula system 50 may further include at least one ring seal 130 (FIG. 24) between the inner cannula 82 and the outer cannula 52.

To insert the cannula system 50, typically a cut is made through the layers of tissue to reach a surgical site in a body cavity, and the cannula system 50 is pushed into the cut to the body cavity. The cannula system 50 generally, and typically the trocar 84 in particular, has a tapered shape in a distal region that helps to push aside the tissue adjacent the cut as the cannula system 50 enters the body. After insertion, the trocar 84 is removed by pulling it out of the system 50 along the longitudinal axis 56. If the living hinge 70 has any spring characteristics, the one or more arms 54 may move from the closed position when the trocar 84 is disengaged. The inner cannula 82 then is advanced within the outer cannula 52 to engage a cam surface 134 on a proximal side of at least one arm 54 with a bearing surface 136 at the distal end of the inner cannula 82. As the inner cannula 82 advances, the bearing surface 136 pushes against the cam surface 134 to rotate the arm or arms 54 about their respective pivot points toward the open position. The inner cannula 82 cannot be advanced before the arm or arms 54 are released or disengaged from the securing elements, in this case by withdrawing the trocar 84. A locking device also may be provided to hold the trocar 84 in position to avoid prematurely releasing the arms 54 from the closed position.

After deploying the one or more arms 54 to the open position, the inner cannula 82 may be further advanced to telescope beyond the distal end of the outer cannula 52. The illustrated arm 54 also has an inner face 140 that generally faces the distal direction when in the open position. In other words, when the inner face 140 of the arm 54 is in the open position, the inner face 140 and the distal end of the outer cannula 52 both generally face the distal direction.

The inner cannula 82 is deployable from a retracted position on a proximal side of the one or more arms 54 to an extended position where a distal region of the inner cannula 82 extends distally beyond its contact with the cam surface 134 and the inner face 140 of at least one arm 54. For example, in one or more embodiments the distal region of the inner cannula 82 may be extended about two centimeters beyond the inner face 140 of at least one arm 54. When the arm or arms 54 are deployed to the open position, they help to keep soft tissue away from the surgical site. By extending the inner cannula 82 beyond the arm or arms 54, the surgical instruments operate on a surgical site that is removed from the arm or arms 54. This also helps to shield the surgical instruments from the ancillary soft tissues that are retracted by the arm or arms 54 in the open position, preventing those tissues from interfering with the surgical procedure, such as the tying of arthroscopic knots in sutures.

An exemplary system 50 has an outer cannula 52 with a length of about eight centimeters, and an inner cannula 82 with a length of about eleven centimeters. The inner cannula 82 can telescope about two centimeters, and the trocar 84 has a length of about seventeen centimeters. The inner diameter of the inner cannula 82 is about eight millimeters, and the outer diameter of the outer cannula 52 is about twelve millimeters. The system 50 includes two arms 54, each of which has a width of about six millimeters adjacent the pivot point, a minimum thickness of about one millimeter, and a length or span of about nine millimeters. In the open position, the arms 54 extend in a direction that is about seventy to one hundred ten degrees relative to the longitudinal axis 56 of the outer cannula 52. The resulting maximum diameter of the outer cannula 52 with the arms 54 deployed in the open position is about thirty millimeters, substantially greater than the twelve-millimeter diameter of the outer cannula 52. Cannula systems with different dimensions also are contemplated as being within the scope of the present invention.

In operation, a method of using such a cannula system for introducing a medical instrument into a patient can be summarized in the following steps: (A) inserting the cannula system 50 into the body of a patient, and (B) deploying the inner member or a part thereof, in this case the trocar 84, to disengage the at least one arm 54 from the inner member and allow the at least one arm 54 to deploy to an open position displaced from the closed position.

An alternative embodiment of a cannula system 200 provided by the invention is shown in FIGS. 11-15. The cannula system 200 is substantially similar to the cannula system 50 (FIG. 1) described above, but the arms are held in the closed position in a different way. As in the system 50 (FIG. 1), this system 200 includes an outer cannula 202 to which at least one arm 204 is pivotally connected. The illustrated embodiment has two arms 204, but as noted above the number of arms may vary without departing from the invention. The arms 204 are deployable from the closed position to an open position by advancing an inner cannula 206 against a cam surface 210 on a proximal side of the arms 204 when the arms are in the closed position. The inner cannula 206 is telescopically received in the outer cannula 202, and is substantially the same as the inner cannula 82 (FIG. 3) described above. The inner cannula and the outer cannula define a cannula assembly when assembled. A trocar 212 is telescopically received in the inner cannula 206, and the inner cannula 206 and the trocar 212 again form the previously-mentioned inner member. Unlike the trocar 84 (FIG. 3) in the previous embodiment, however, this trocar 212 provides a unique structure and functionality.

Figure 16:
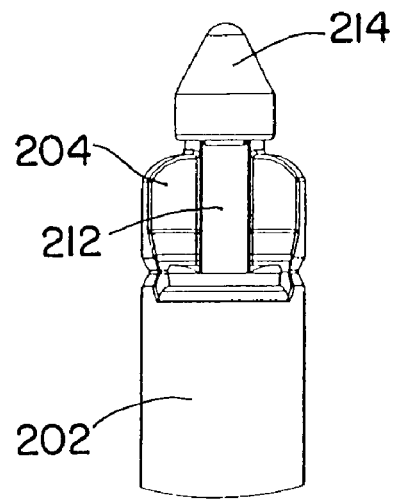
FIG. 16 is an enlarged side view of an alternative distal region of the cannula system of FIG. 11.
Figure 17:
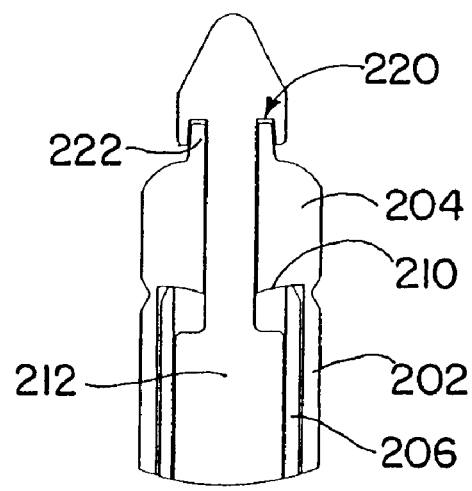
FIG. 17 is a cross-sectional view of the alternative embodiment of FIG. 16.
Figure 18:
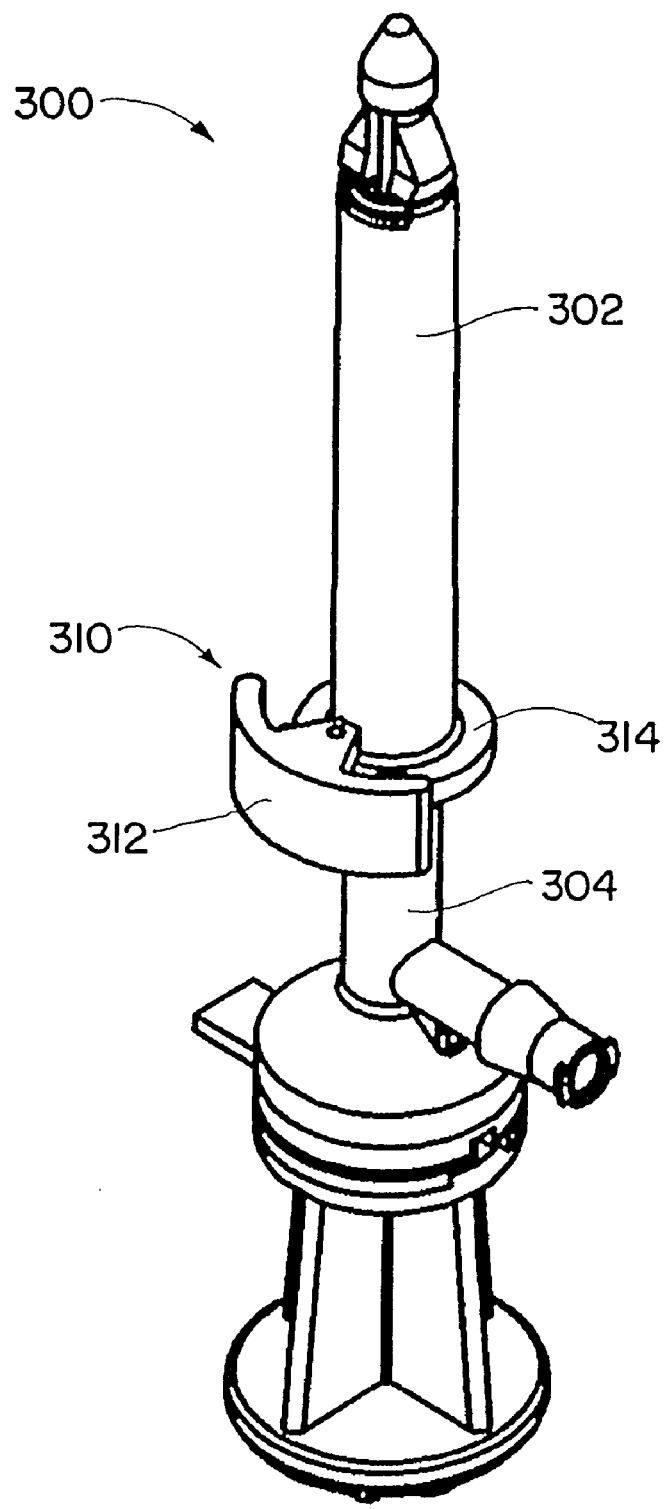
FIG. 18 is a perspective view of another alternative embodiment of a cannula system provided by the present invention.
Figure 19:
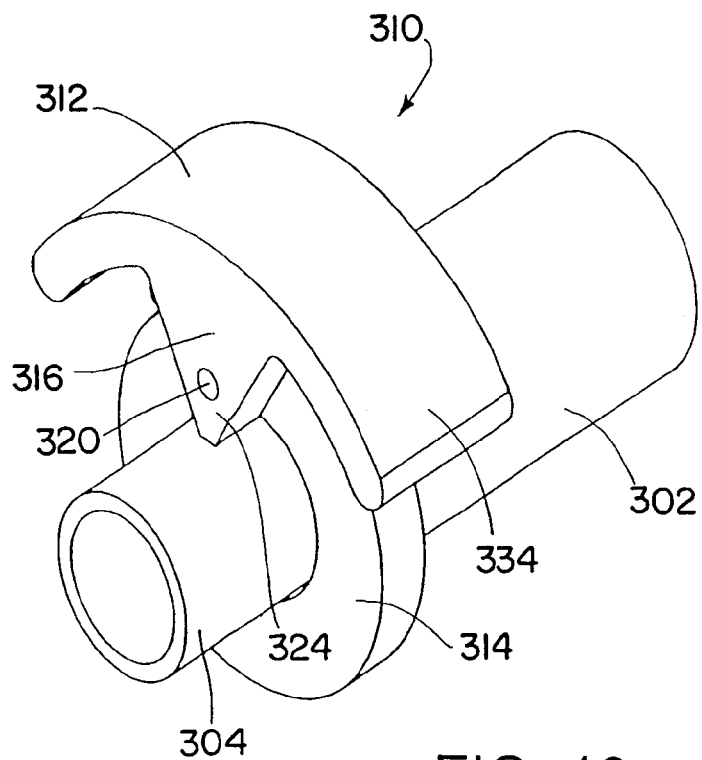
FIG. 19 is an enlarged perspective view of locking mechanism portion of the cannula system of FIG. 18.
Figure 20:
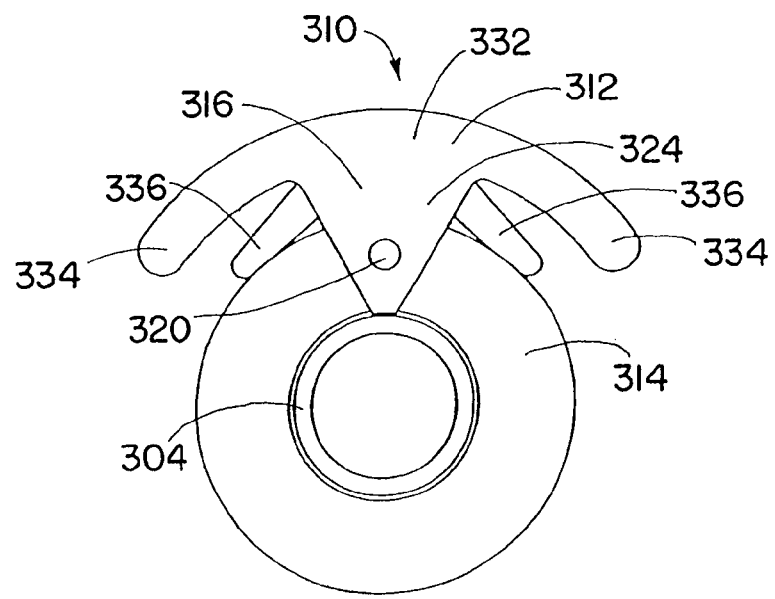
FIG. 20 is an end view of the locking mechanism portion of FIG. 19.
Figure 21:
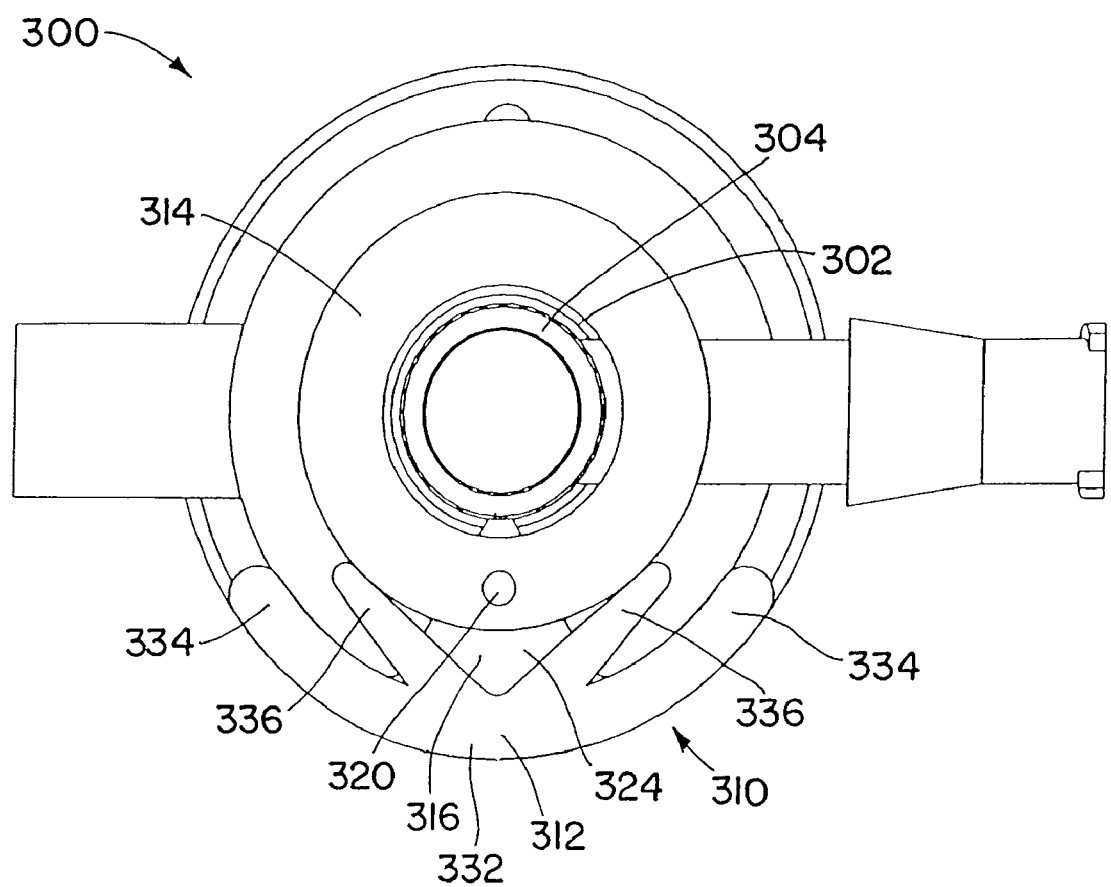
FIG. 21 is a cross-sectional view of the cannula system of FIG. 18.
Figure 22:
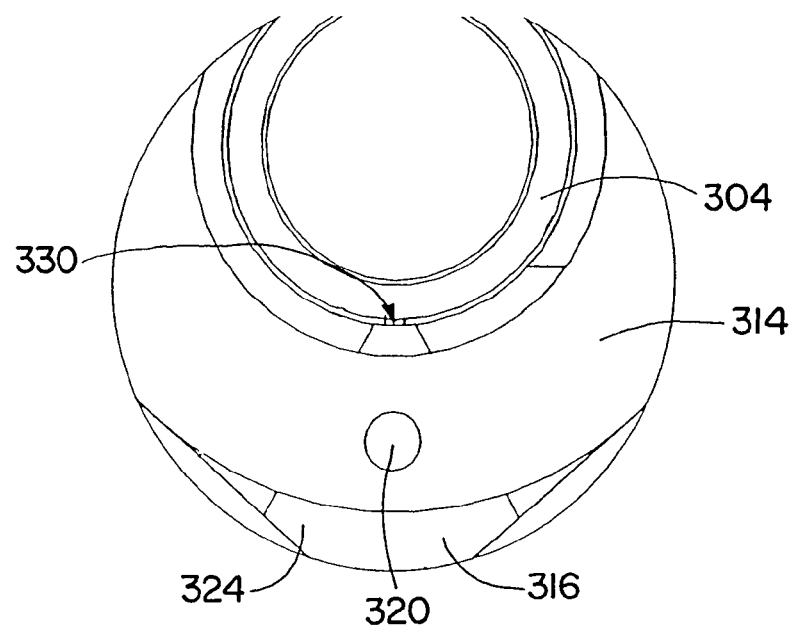
FIG. 22 is an enlarged view of a portion of FIG. 21.

In particular, the trocar 212 has an enlarged tip portion 214 at a distal region thereof that generally has a cone shape. The arm or arms 204 generally continue the tapered shape of the distal end of the cannula system 200 from the trocar 212 to the outer diameter of the outer cannula 202. Alternatively, however, the arm or arms 204 may have a different outer shape with a sharper transition to a larger diameter, as seen in FIGS. 16 and 17, for example.

Returning to FIGS. 11-15, the at least one element that holds the one or more arms 204 in the closed position may include a recess 220 in a proximal side of the enlarged tip portion 214. The recess 220 may take the form of a continuous groove or circumferentially spaced-apart slots that can be aligned with corresponding elements of the arms 204 so that the arms will mate with the slots. In the illustrated embodiment, a tab portion 222 in a distal region of at least one arm 204 is received in the recess 220 to hold the arm 204 in the closed position. Thus in the closed position the trocar 212 encapsulates the distal ends of the arms 204 in the illustrated embodiment. Unlike the previous embodiment, in this embodiment the trocar 212 must be advanced in the distal direction to disengage the one or more arms 204, which must move from the closed position before the trocar 212 can be removed through the inner cannula 206.

A locking device in the form of a removable spacer 230 holds the trocar 212 in place relative to the inner cannula 206 until the arms 204 are ready to be deployed. The illustrated spacer 230 has a pull tab 232 that facilitates grasping and removing the spacer 230, and similar arrangements are commonly found on tamper-resistant bottle caps. Upon removal of the spacer 230, the trocar 212 or other inner member can be advanced to release the arm or arms 204 from the recess 220. As the inner member disengages from the one or more arms 204, the inner cannula 206 is free to advance relative to the outer cannula 202 to engage and deploy the arms 204 to the open position. Once the arms are out of the way, the trocar 212 can be retracted through the through hole in the inner cannula 206 and removed from the system 200.

A method of using such a cannula system 200 for introducing a medical instrument into a patient may include the following steps: inserting the cannula system 200 into the body of a patient, such as a joint like the knee, shoulder, or hip, and deploying the inner member, such as the trocar 212, into the body of the patient to disengage at least one arm 204 from the inner member and allow the arm or arms 204 to deploy toward an open position displaced from the closed position. The one or more arms 204 can move out of the closed position under the influence of a bias force away from the closed position, or the inner cannula can be advanced to deploy the one or more arms from the closed position. The trocar 212 then can be withdrawn past the arms 204 and through the inner cannula 206.

The method further may include the steps of: advancing the inner member in the distal direction to disengage at least one arm 204, and then advancing in the distal direction an inner cannula 206, telescopically received in the outer cannula 202, to deploy the one or more arms to the open position before retracting and removing the inner member through the inner cannula 206 in the proximal direction. The method also can include the step of securing the inner cannula 206 relative to the outer cannula 202, including securing the inner cannula 206 in a fixed position relative to the outer cannula 202. The method also may include the steps of retracting the inner cannula 206 to release the arm or arms 204 from the open position and then withdrawing one or both of the outer cannula 202 and the inner cannula 206 from the patient.

In use, the surgeon inserts the cannula system 200 into the patient at the surgical site, pulls the pull tab 232 and removes the spacer 230, thereby releasing the locking device. While holding the outer cannula 202 and the inner cannula 206 together in one hand, the other hand can push the trocar 212 further forward in the distal direction into the body, thereby releasing the arms 204 from the locking device provided in the distal region of the trocar 212. Then, while grasping the outer cannula 202, the inner cannula 206 is pushed forward until the arm or arms 204 have been rotated sufficiently out of the way that the trocar 212 can be removed from the inner cannula 206. The inner cannula 206 can then be advanced to deploy the arms 204 the rest of the way to the fully open position. The inner cannula 206 may be advanced farther to deploy a distal region of the inner cannula 206 beyond the arms 204 and distal end of the outer cannula 202.

Figure 56:
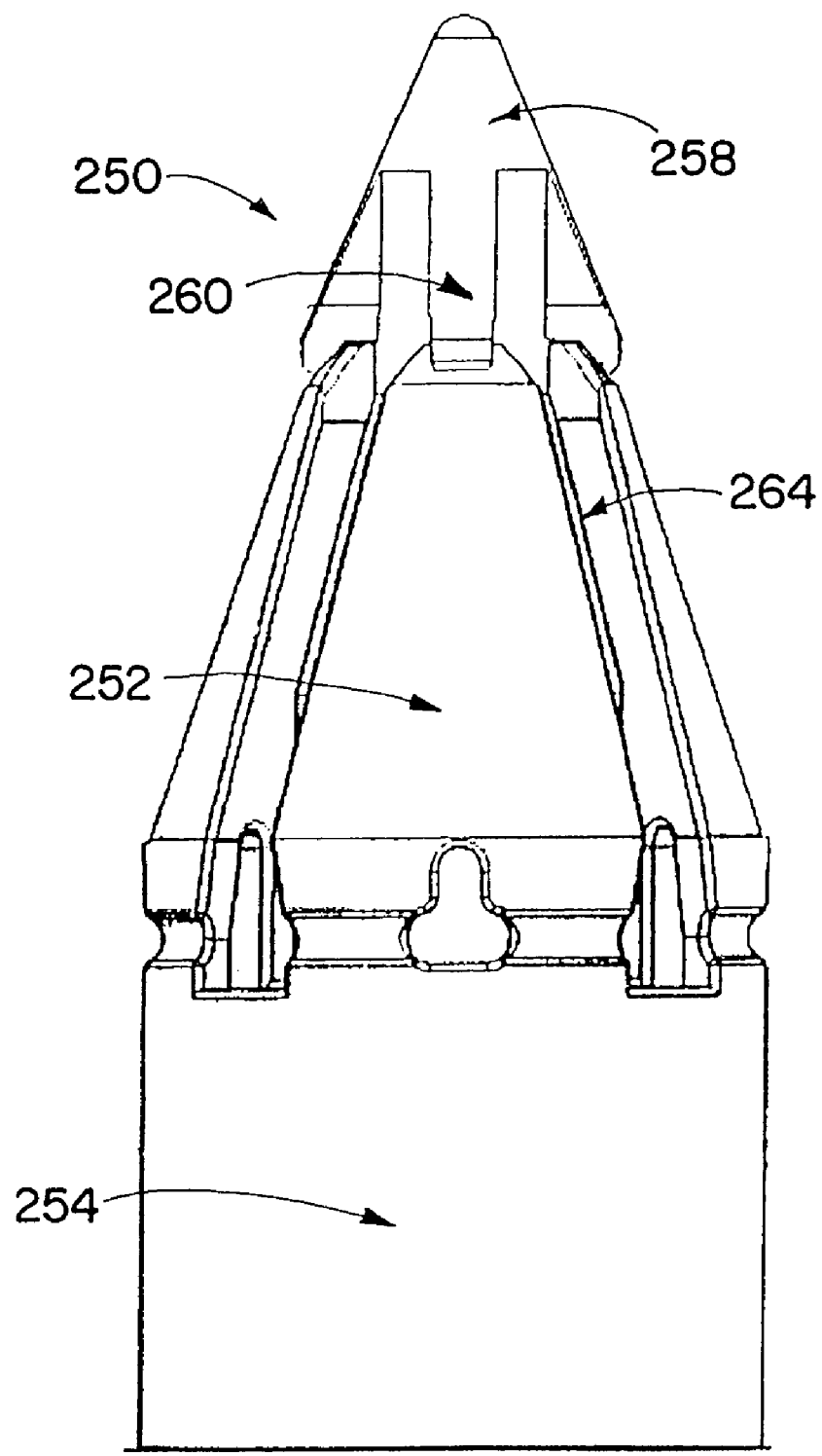
FIG. 56 is a side view of a distal region of yet another embodiment of a cannula system provided in accordance with the present invention with an inner member in an engaged position.
Figure 57:
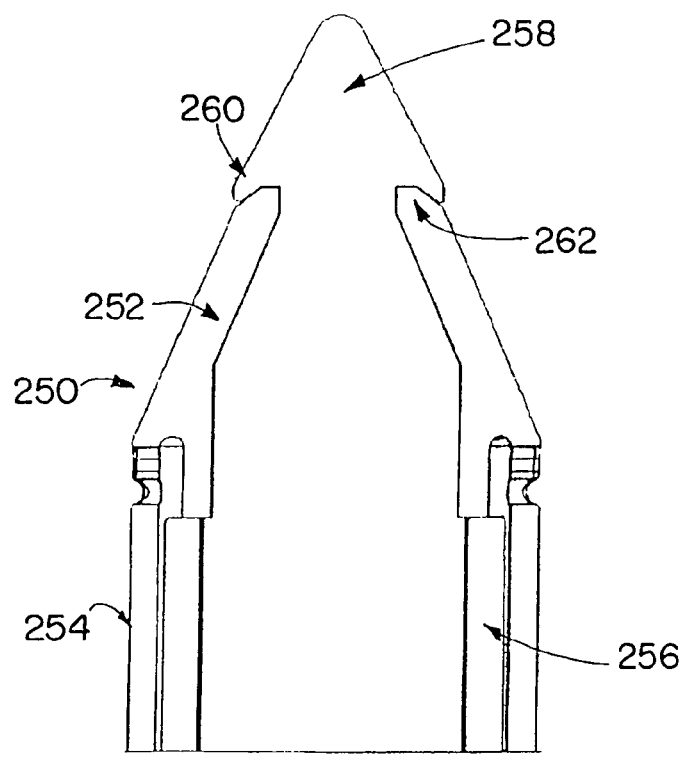
FIG. 57 is a cross-sectional view of the cannula section of 56.
Figure 58:
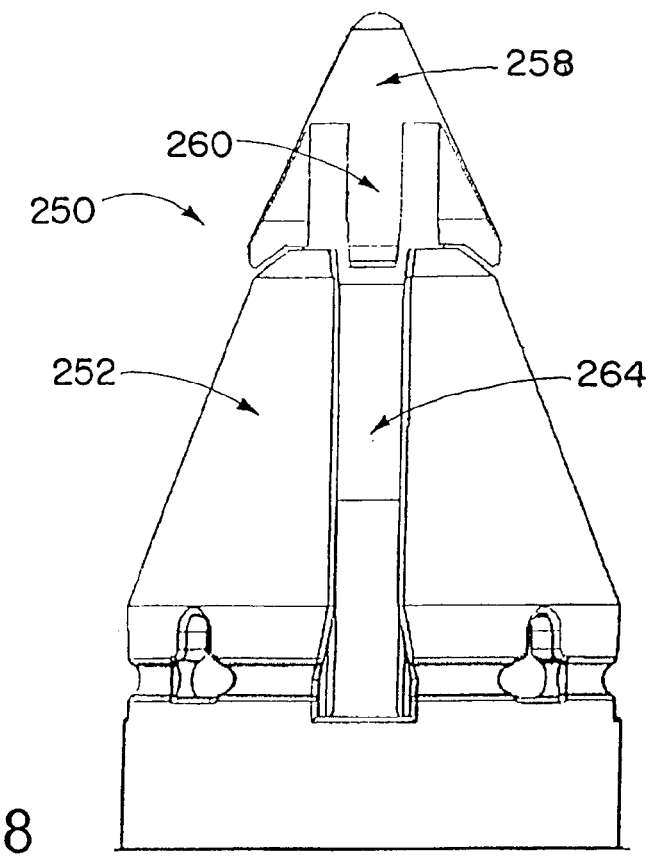
FIG. 58 is a side view of the cannula system of FIG. 56 with the inner member in a disengaged position.
Figure 59:
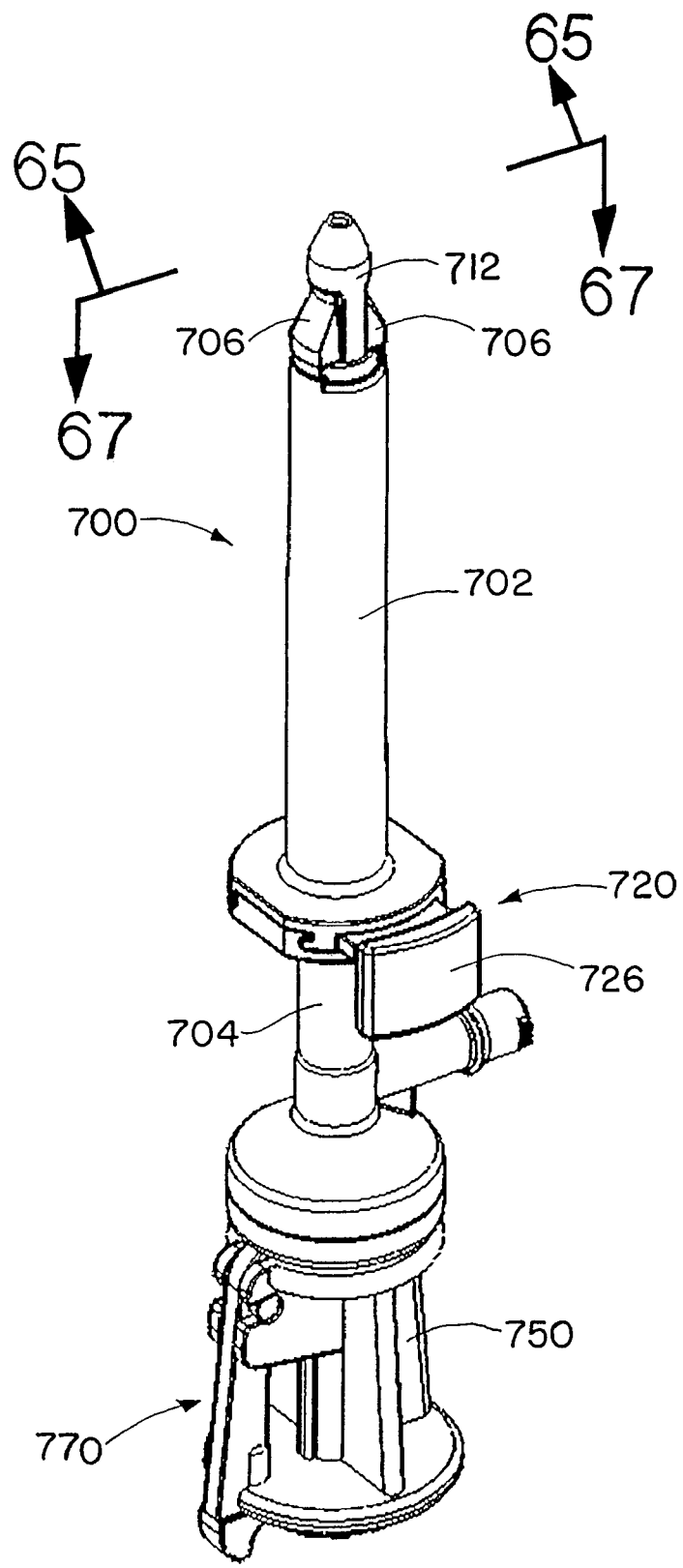
FIG. 59 is a perspective view of yet another cannula system provided in accordance with the present invention.
Figures 60, 61:
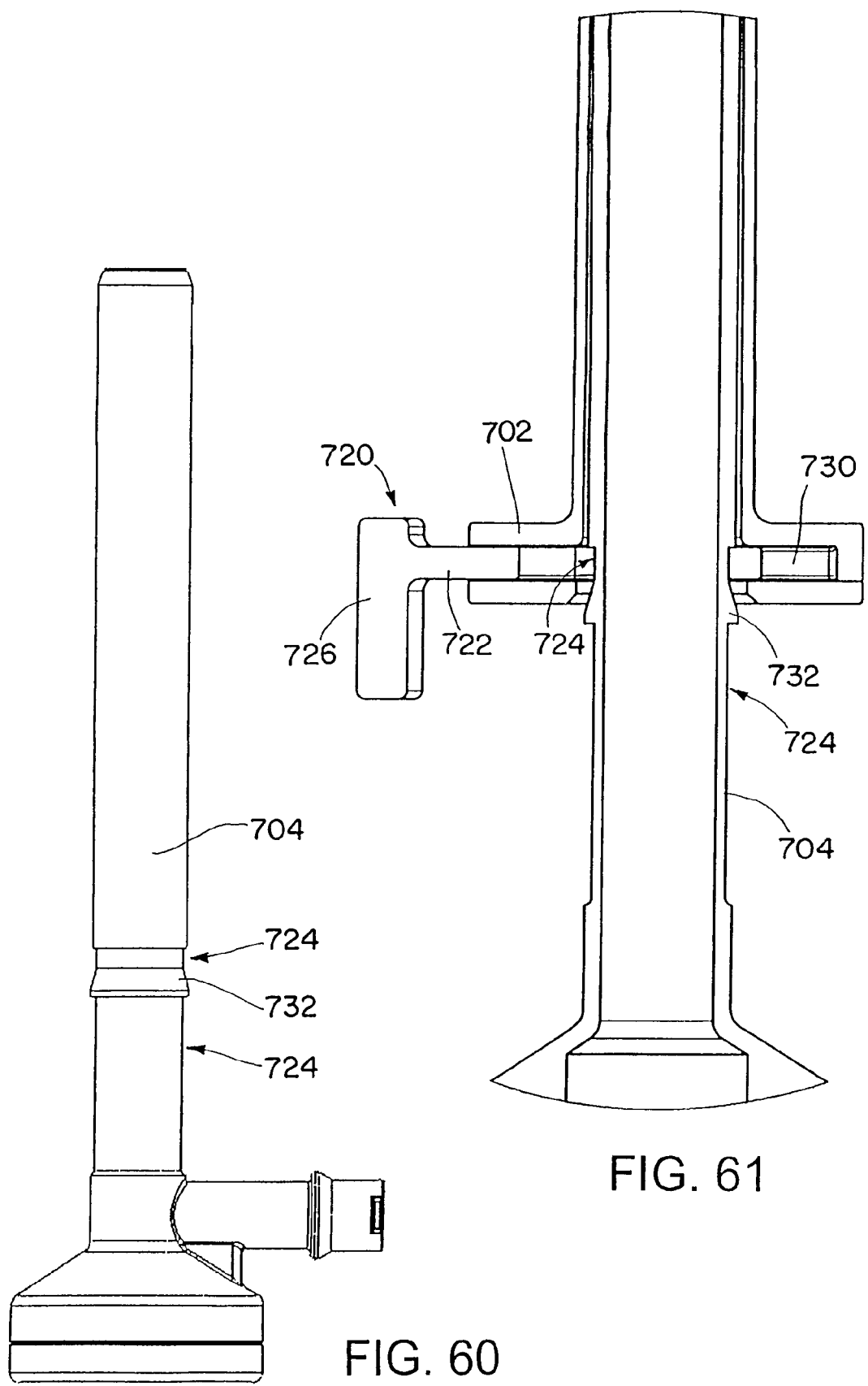
FIG. 60 is a side elevation view of the inner cannula portion of the cannula system of FIG. 59.
FIG. 61 is an enlarged cross-sectional side elevation view of a portion of the cannula system of FIG. 59.
Figure 62:
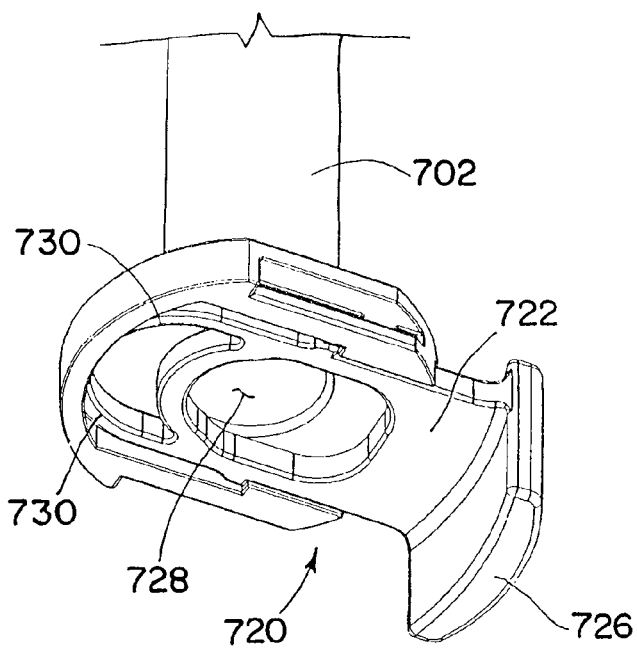
FIGS. 62 and 63 are different perspective views of a proximal end of an outer trocar portion of the cannula system of FIG. 59.
Figure 63:
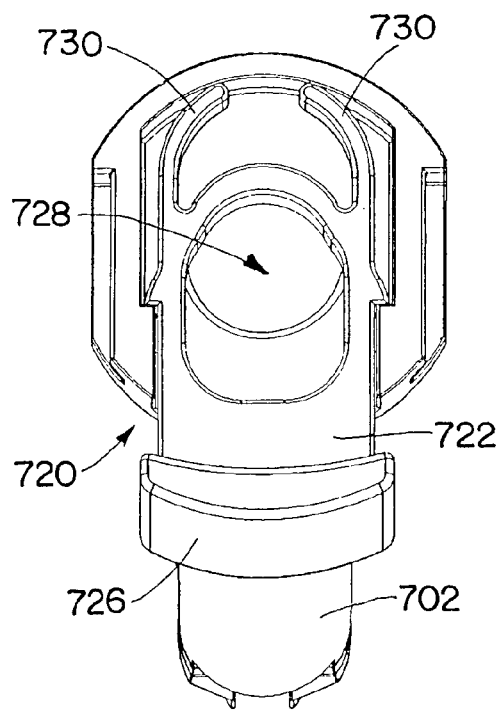

Another embodiment, shown in FIGS. 56-58 provides yet another way to hold the one or more arms in the closed position. In this cannula system 250, which also includes one or more arms 252 connected at a distal end of an outer cannula 254, an inner cannula 256 is telescopically received in the outer cannula 254, and a trocar 258 is telescopically received in the inner cannula 256.

The trocar 258 includes elements that engage the distal end of at least one arm 252. In this case, the trocar 258 has one or more hooked fins 260 in an enlarged distal region. The enlarged distal region of the trocar 258 generally defines a cone shape with an outer surface of the trocar tapering toward a point in the distal direction. Each fin 260 typically has a relatively larger diameter at a proximal end with at least one adjacent recessed portion with a smaller diameter. The proximally-facing side of at least one fin 260 includes a recess 262 that defines a proximally-facing hook into which a distal end of an arm 252 is received. The trocar 258 thus engages and holds the arm or arms 252 in the closed position.

To disengage the one or more arms 252, the trocar 258 may be advanced in the distal direction as in the previous embodiment, but generally the trocar 258 may be immediately or subsequently rotated to align the one or more fins 260 with corresponding slots 264 adjacent the one or more arms 252, typically in the space between two arms 252. The slots 264 extend into the inner cannula 256 and/or outer cannula 254, whereby the trocar 258 may be withdrawn through the inner cannula 256 only when the one or more fins 260 are aligned with those slots 264. Corresponding indicia in a proximal region of the trocar 258 may be used to align the fins 260 with the slots 264 to withdraw the trocar 258 after insertion of the cannula system 250 into the patient's body.

Figure 11:
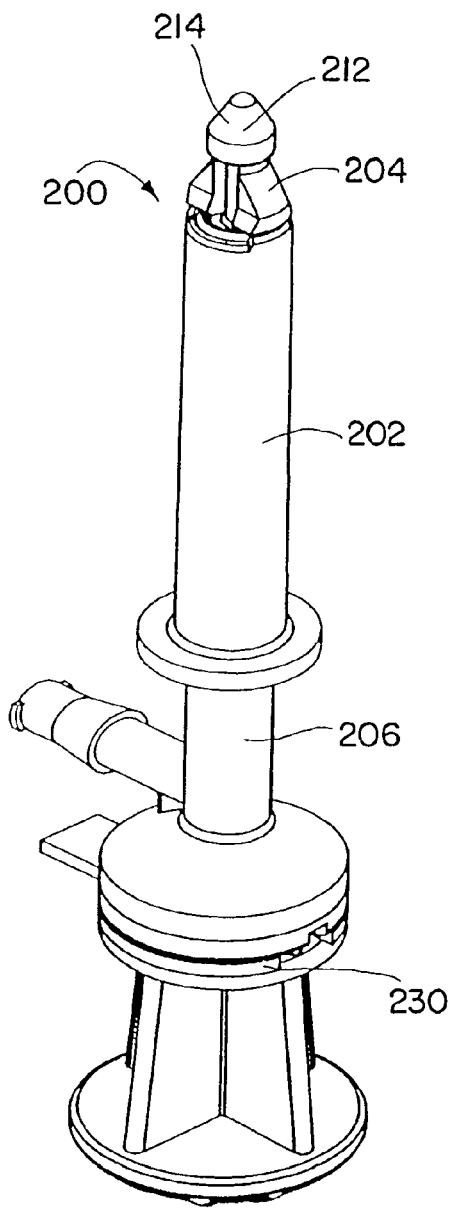
FIG. 11 is a perspective view of an alternative embodiment of the cannula system provided in accordance with the present invention.
Figure 12:
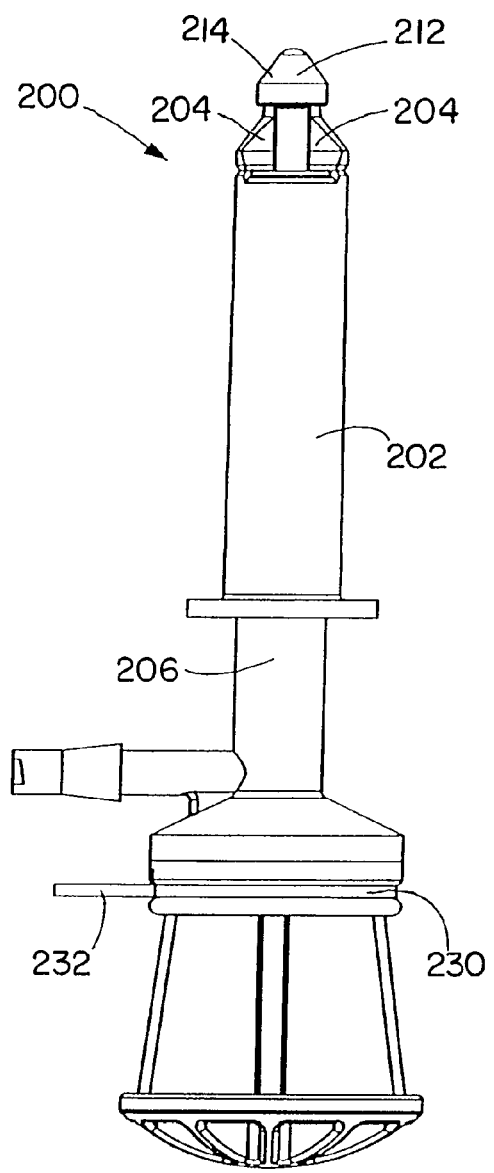
FIG. 12 is a side view of the cannula system of FIG. 11.
Figure 13:
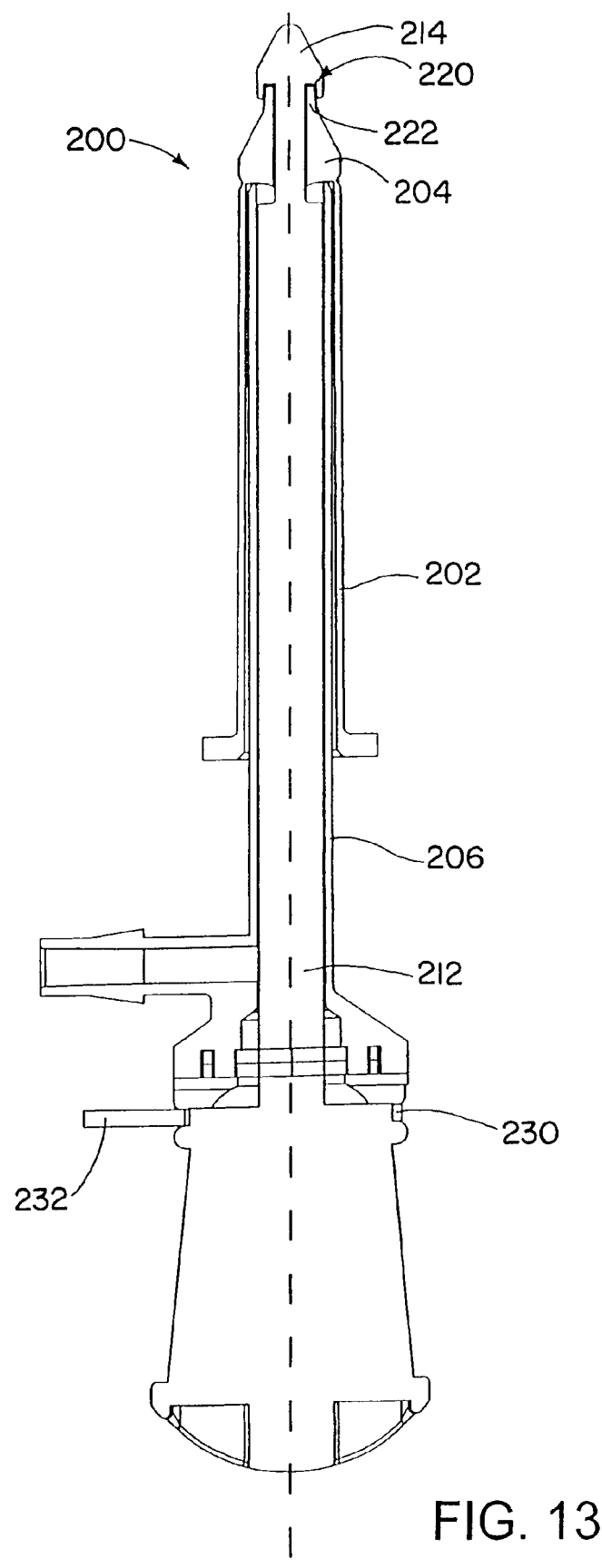
FIG. 13 is a cross-sectional elevational view of the cannula system of FIG. 12.
Figure 14:
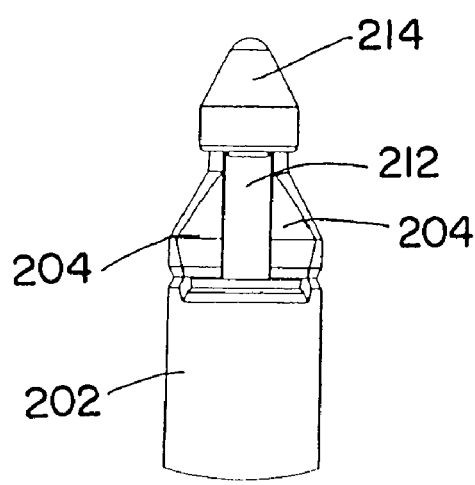
FIG. 14 is an enlarged side view of a distal region of the cannula system of FIG. 12.
Figure 15:
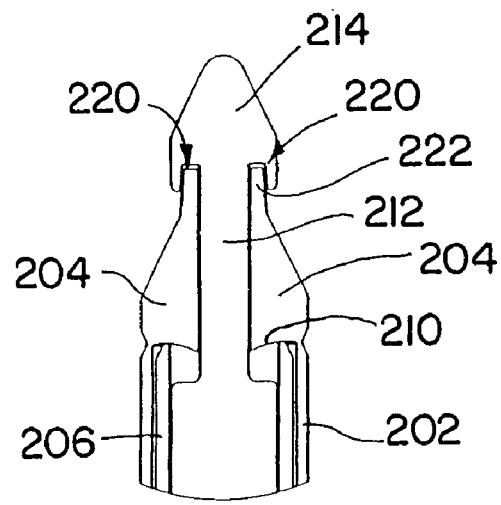
FIG. 15 is an enlarged view of a distal region of the cannula system of the cross-sectional view of FIG. 13.

Another variation on the cannula system 200 of FIG. 11 is shown in FIGS. 18-23. The cannula system 300 shown in FIGS. 18-23 also includes an outer cannula 302 and an inner cannula 304 telescopically received in the outer cannula 302 to form a cannula assembly. The outer cannula 302 has a locking mechanism 310 that could be employed in any of the cannula systems described herein. The locking mechanism 310 includes a toggle 312 pivotally attached to a flange 314 in a proximal region of the outer cannula 302.

The toggle 312 has a pivot portion 316 connected to the outer cannula flange 314 by a pivot pin 320 that defines a pivot axis about which the toggle 312 can rotate. The pivot portion 316 has an approximately J-shape and extends around the outer cannula flange 314 with the pivot pin 320 connecting the legs of the J shape. The shorter leg 322 of the pivot portion 316 is on a distal side of the outer cannula flange 314, and the longer leg 324 is on a proximal side of the outer cannula flange 314. The end of the longer leg 324 includes a plurality of small teeth 330 that engage the outer surface of the inner cannula 304 when in a locked position to hold the outer cannula 302 in a fixed position relative to the inner cannula 304. A central portion 332 interconnects the shorter and longer legs 322 and 324 and is radially outwardly spaced from the pivot pin 320 and the edge of the outer cannula flange 314.

The toggle 312 also has arms extending outwardly from the central portion 332. The arms include control arms 334 that control the locking and releasing action of the mechanism 310, and spring arms 336 that bear against the outer cannula flange 314 from the central portion 332. The control arms 334 generally extend on an arc radially outward from the axis of the pivot pin 320. The spring arms 336 bias the toggle 312 to the locked position. The locking mechanism 310 can be operated with one hand, such as the hand holding the outer cannula 302 while the other hand moves the inner cannula 304 relative to the outer cannula 302.

By pressing either one of the control arms 334, the toggle 312 will rotate in the direction pushed to unlock the inner cannula 304 from the outer cannula 302. The toggle 312 thus has two unlocked positions with the default locked position in between. Upon releasing the control arm 334 the spring arms 336 will move the toggle 312 back to the center position, engaging the teeth 330 against the outer surface of the inner cannula 304 to hold it in place.

Another embodiment of a cannula system 350 provided by the present invention is shown in FIGS. 25 and 26. In this embodiment, the cannula system 350 includes an outer cannula 352 with one or more arms 354, an inner cannula 356 telescopically received in the outer cannula 352, and a trocar 360 telescopically received in the inner cannula 356. The trocar 360 in this embodiment also is tubular, with a through hole 362 extending along a longitudinal axis 364 of the cannula system 350.

Sometimes a guide wire or switching stick is inserted into the body cavity at the desired angle to help guide the cannula system into the desired position. The through hole 362 in the trocar 360 allows the cannula system 350 to be guided into position by threading the guide wire or switching stick through the through hole 362 in the trocar 360. The cannula system 350 is fed along the guide wire or switching stick into the desired position relative to the surgical site. The guide wire or switching stick can then be removed through that passage (the through hole 362) or removed from the cannula system 350 together with the trocar 360.

Turning now to FIGS. 27-34, various devices are shown, each of which includes an outer cannula 400, 410, 420, and 430, to which one or more arms 402, 412, 422, and 432 are connected. As mentioned above, the one or more arms attached to the outer cannula are deployed from the closed position to the open position by advancing an inner cannula (not shown) against cam surfaces 404, 414, 424, and 434 of the arms that extend into the path of the inner cannula inside the outer cannula. The pivot point 405, 415, 425, and 435 for each arm is defined by a living hinge 406, 416, 426, and 436, and in these embodiments the cam surface extends inside the outer cannula to a point on a proximal side of the pivot point. Each of these embodiments include four arms, only two of which are visible in any given figure.

In FIGS. 27-32 the outer surface of the arms 402, 412, and 422 generally define a cone shape, while the arms 432 in FIGS. 33 and 34 define a hemispherical shape. Both shapes provide a surface with a gradually increasing diameter that guides tissue from the relatively smaller diameter distal end to the relatively larger diameter of the outer cannula as the cannula system is inserted into the patient. In each of these embodiments, a line perpendicular to the longitudinal axis has been drawn approximately through the pivot point of the living hinge. Each living hinge owes its flexibility to the use of a resilient material and to different ways of reducing the amount of material at the pivot point.

Figure 27:
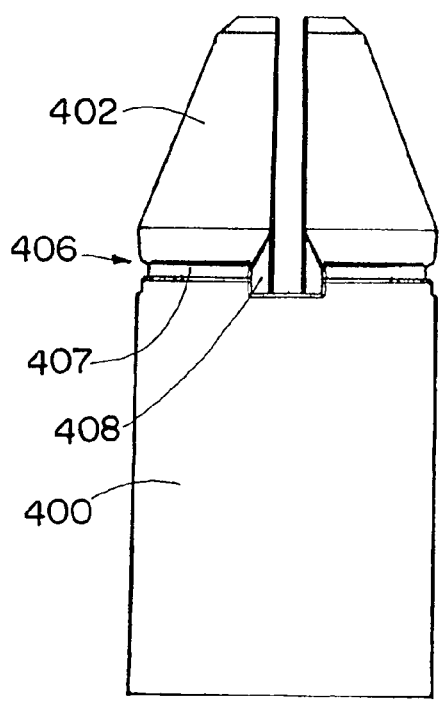
FIG. 27 is an elevational view of a distal region of an outer cannula provided by the present invention.
Figure 28:
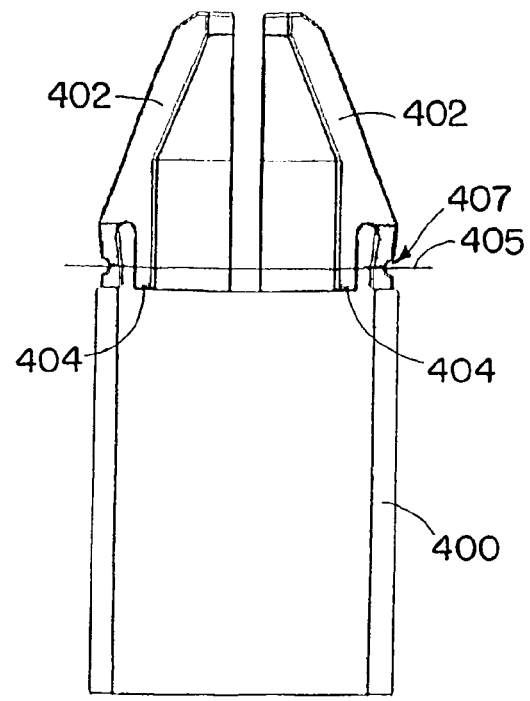
FIG. 28 is an elevational cross-sectional view of the outer cannula of FIG. 27.
Figure 29:
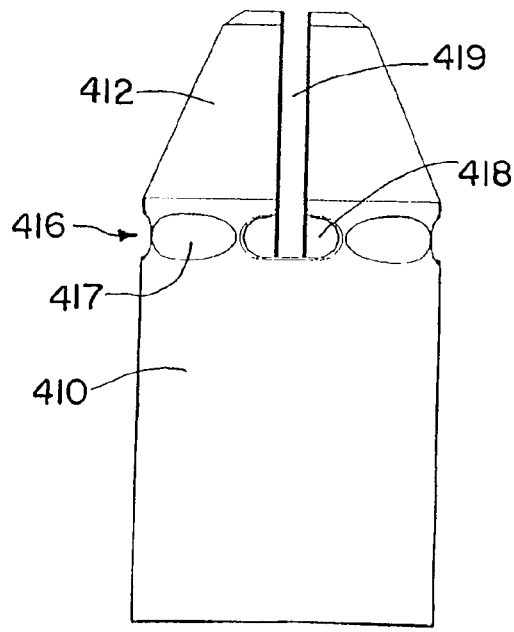
FIG. 29 is an elevational view of a distal region of an outer cannula provided by the present invention.
Figure 30:
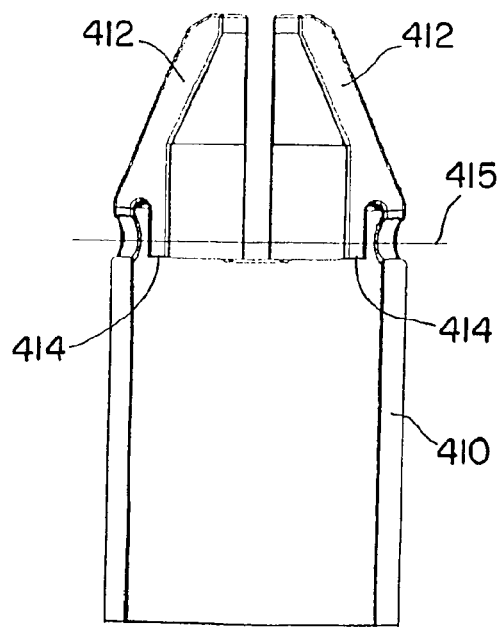
FIG. 30 is an elevational cross-sectional view of the outer cannula of FIG. 29.
Figure 37:
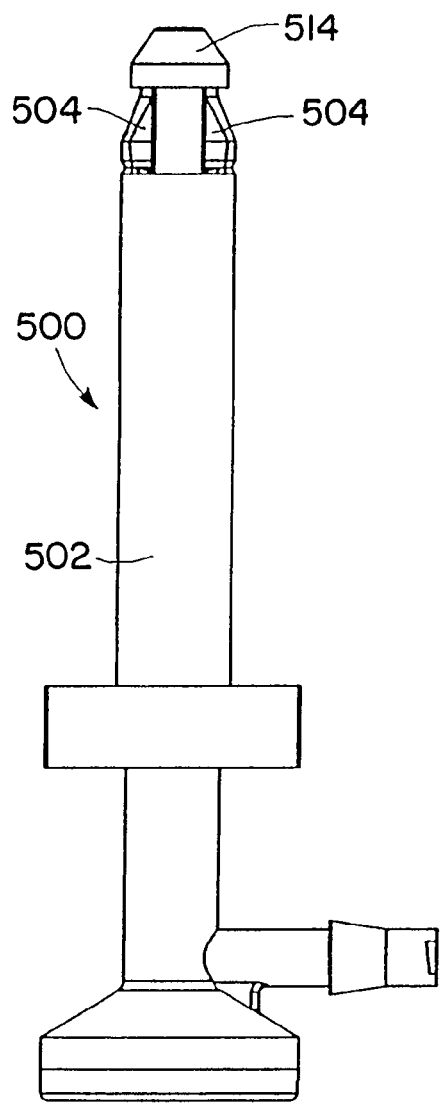
FIG. 37 is a side view of the cannula system of FIG. 35.
Figure 38:
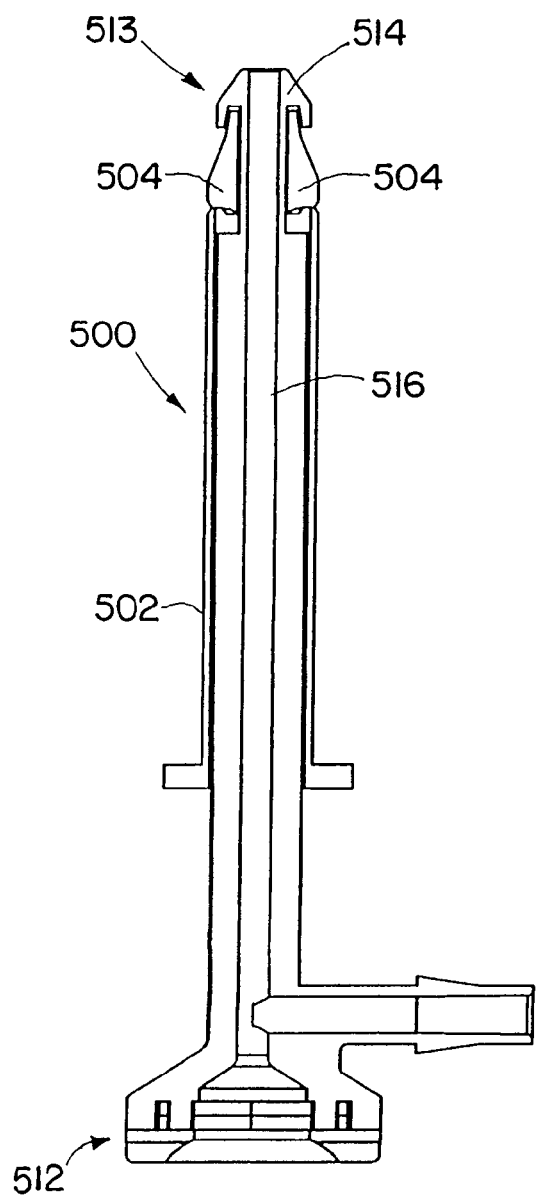
FIG. 38 is a cross-sectional view of the cannula system of FIG. 37.
Figure 39:
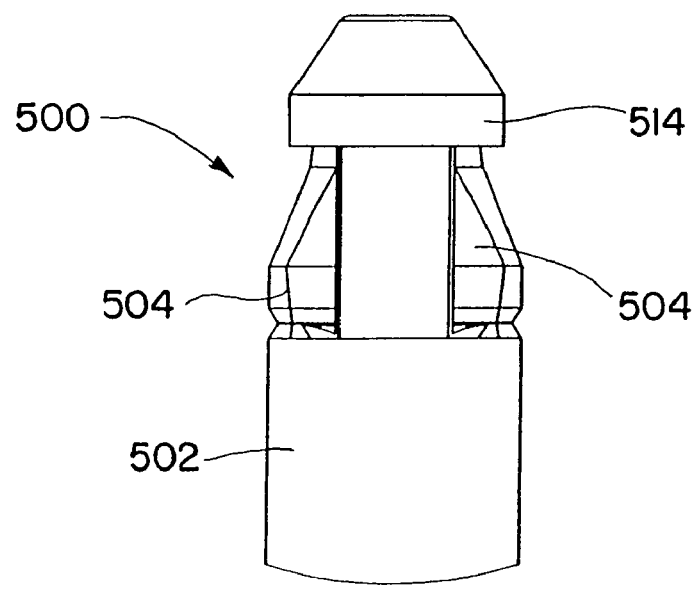
FIG. 39 is an enlarged view of distal region of the cannula system of FIG. 37.
Figure 40:
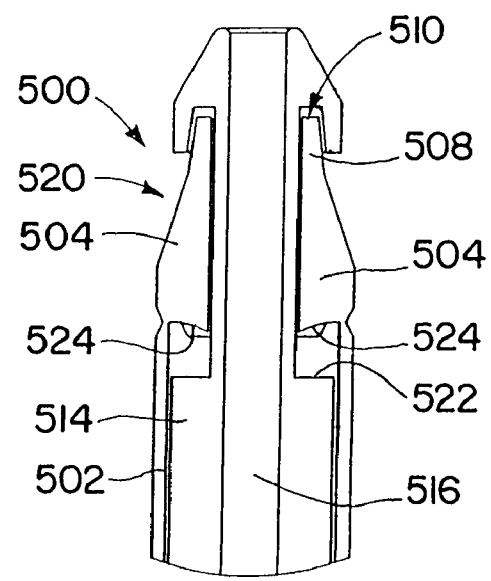
FIG. 40 is a cross-sectional view of a distal region of the cannula system of FIG. 39.
Figure 41:
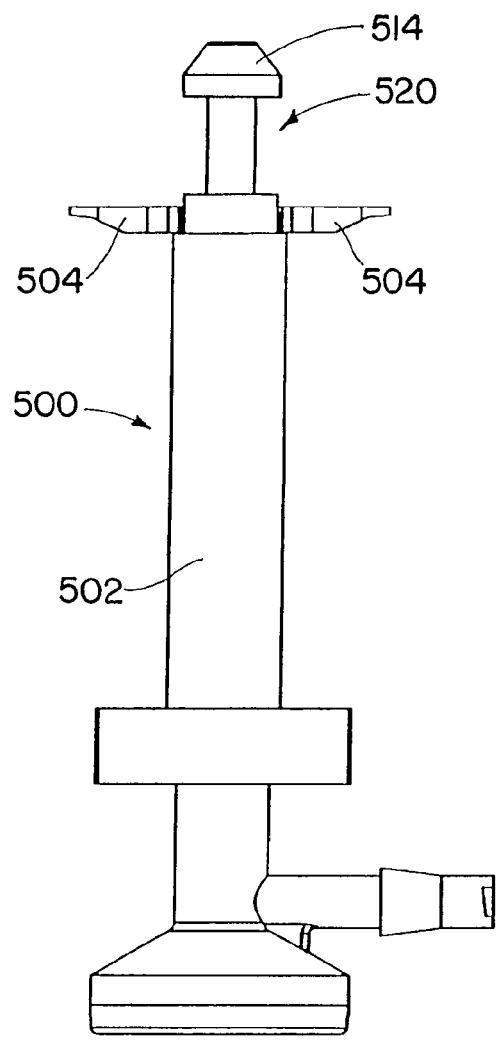
FIG. 41 is a side view of the cannula system of FIG. 36.
Figure 42:
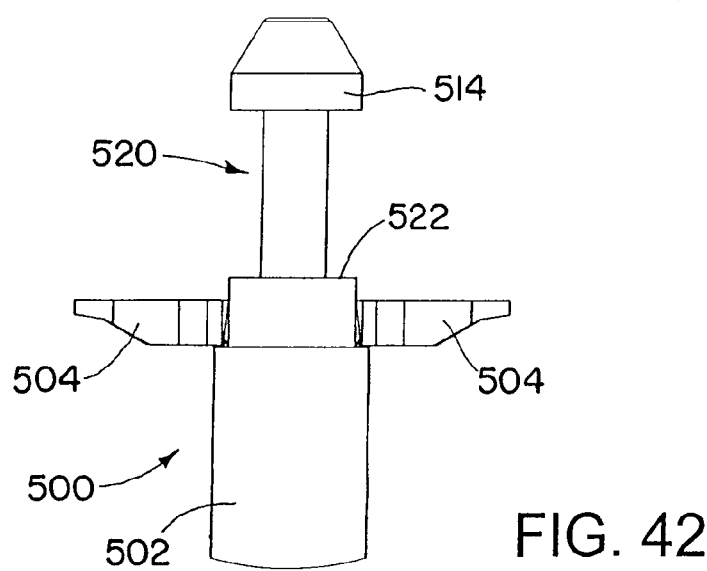
FIG. 42 is an enlarged view of distal region of the cannula system of FIG. 41.
Figure 43:
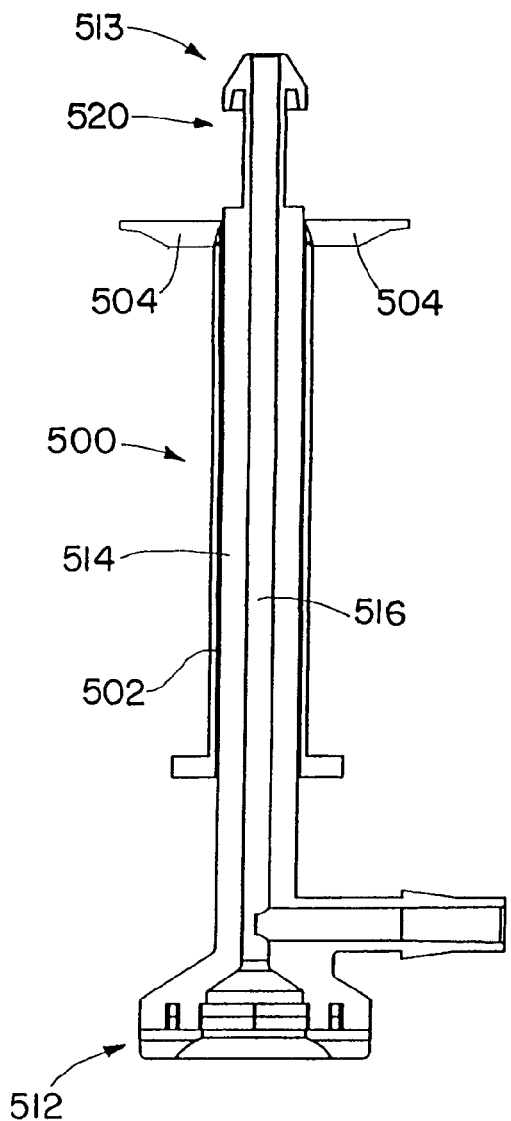
FIG. 43 is a cross-sectional view of the cannula system of FIG. 41.
Figure 44:
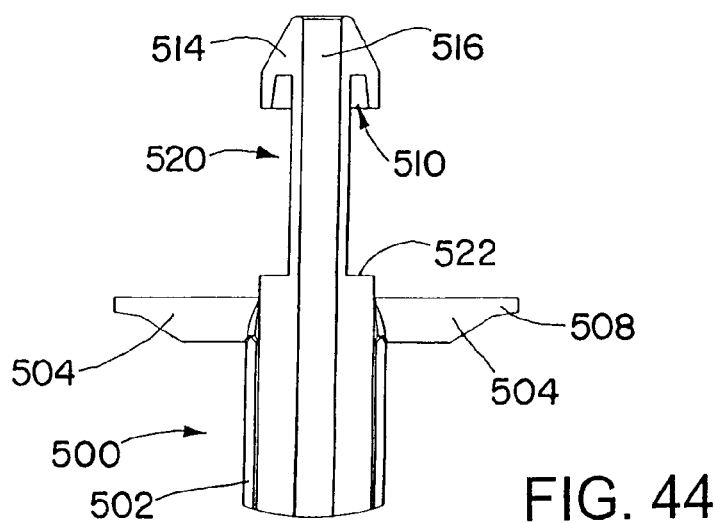
FIG. 44 is an enlarged view of a distal region of the cannula system of FIG. 43.
Figure 45:
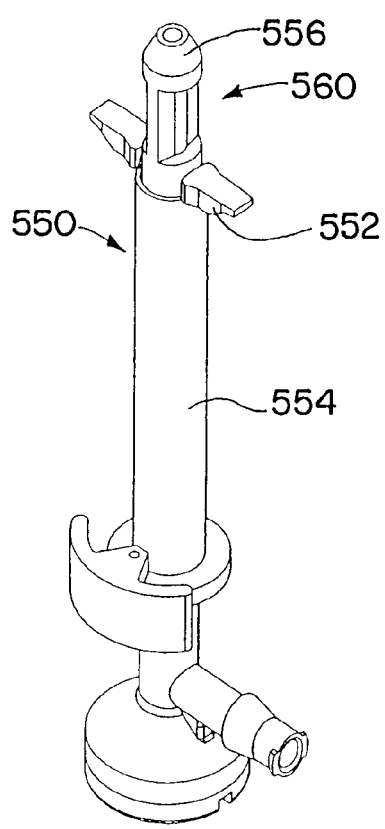
FIG. 45 is a perspective view of an alternative embodiment of a cannula system provided in accordance with the present invention with an inner member distally extended.
Figure 46:
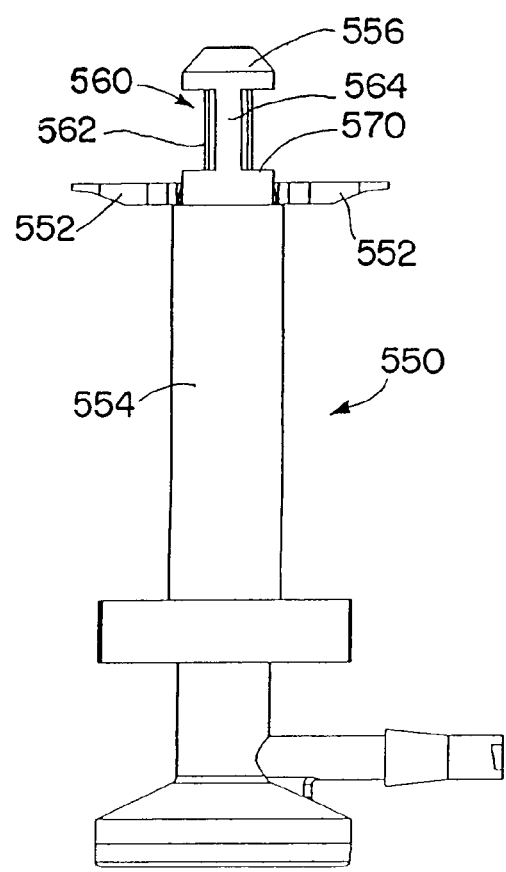
FIG. 46 is a side view of the cannula system of FIG. 45.
Figure 47:
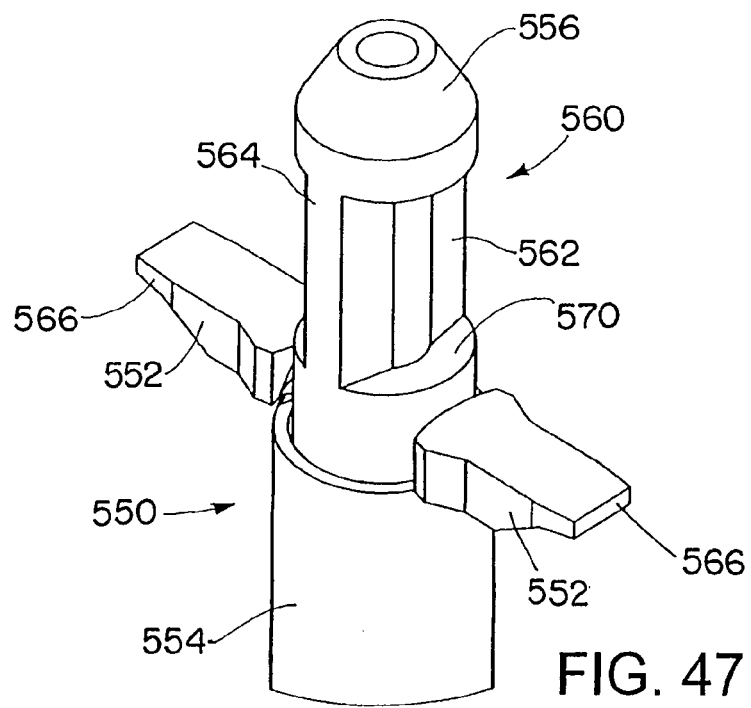
FIG. 47 is an enlarged view of the distal view of the cannula system of FIG. 45.

In FIGS. 27 and 28, the living hinge 405 is formed by a circumferential groove 407 and enlarged notches 408 between adjacent arms 402. In FIGS. 29 and 30, a circumferential necklace of elliptical recesses 417 form the living hinge 416. Another elliptical recess 418 is aligned with a slot 419 between adjacent arms 412. FIGS. 31 and 32 also employ a circumferential groove 427, similar to that of FIGS. 27 and 28, in combination with an elliptical recess 428 between adjacent arms 422. And in FIGS. 33 and 34 the living hinge 436 is formed by circumferential slots 437 that define a pair of circumferentially-spaced legs 438 that connect each arm 432 to the outer cannula 430.

Referring now to FIGS. 35 through 44, and initially FIGS. 35 and 37 through 40, yet another embodiment of a cannula system 500 provided in accordance with the present invention is shown. In this embodiment the cannula system 500 generally, and particularly the outer cannula 502, is substantially similar to the cannula system 200 and the outer cannula 202 shown in FIGS. 11 through 15, with the addition of the locking mechanism 310 of FIG. 18. As in FIG. 11, one or more arms 504 are pivotally connected to a distal end of the outer cannula 502 and have tab portions 508 at distal ends thereof that are received in a circumferential slot 510 that faces a proximal end 512 of the cannula system 500 opposite the distal end 513.

In this embodiment, the inner cannula 206 and the trocar 212 disclosed in the embodiment of FIG. 11 have now been combined into a single inner member 514. The inner member 514 is telescopically received in the outer cannula 502, has a tapered distal end and a through hole 516 extending longitudinally therethrough for surgical instruments, a trocar, a guide wire, a switching stick, suction and irrigation, etc. The inner member 514 also includes an arm-engaging recessed portion 520 near a distal end of the inner member 514 that has a reduced diameter relative to the adjacent proximal and distal portions of the inner member 514. At a distal side of the recessed portion 520 the inner member 514 includes the proximally-facing slot 510 for engaging the tab portions 508 on the arms 504. And in the closed position the one or more arms 504 are received within that recessed portion 520 with their tab portions 508 received within the slot 510 in the inner member 514. On a proximal side of the recessed portion 520, the inner member 514 provides a shoulder 522 for engaging cam surfaces 524 on the one or more arms 504 to deploy the arms as the inner member 514 is proximally advanced.

The recessed portion 520 of the inner member 514 is approximately the same length as or longer than the length of an arm 504 so that the inner member 514 can be advanced to disengage the tab portions 508 on the arm or arms 504 from the slot 510 before deploying the at least one arm 504 from the closed position to the open position, which is shown in FIGS. 36 and 41 through 44. The recessed portion 520 receives the arm or arms 504 in the closed position to minimize the diameter of the cannula system 500 in the closed position. The recessed portion 520 of the inner member 514 extends circumferentially around the inner member 514. Consequently, the angular position of the inner member 514 is not critical to engaging or disengaging the inner member 514 relative to the one or more arms 504.

That is not the case for the cannula system 550 shown in FIGS. 45 through 50, however. This cannula system 550 also has one or more arms 552 connected to a distal end of an outer cannula 554 and a combined trocar and inner cannula in the form of a similar inner member 556 telescopically received in the outer cannula 554. In this embodiment, the inner member 556 has a circumferentially discontinuous recessed portion 560 with at least one reduced diameter recess 562 defined by one or more ribs 564 that extend out to a larger diameter. The recess 562 is sized to receive at least one arm 552 in the closed position. As in the previous embodiment, the inner member 556 engages tab portions 566 of the one or more arms 552 in a proximally-facing slot (not shown) at a distal end of the recess 562. Distally advancing the inner member 556 disengages the tab portion of the arm 552 from the slot. Continued distal advancement engages a shoulder 570 at a proximal side of the recess 562 against a cam surface at a proximal side of at least one arm 552 in the closed position to deploy the arm or arms 552 toward the open position.

Figure 50:
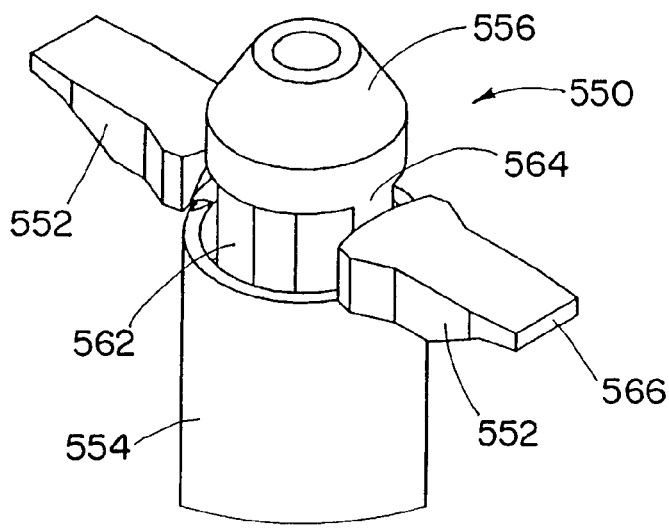
FIG. 50 is an enlarged view of a distal region on the cannula system of FIG. 48.
Figure 51:
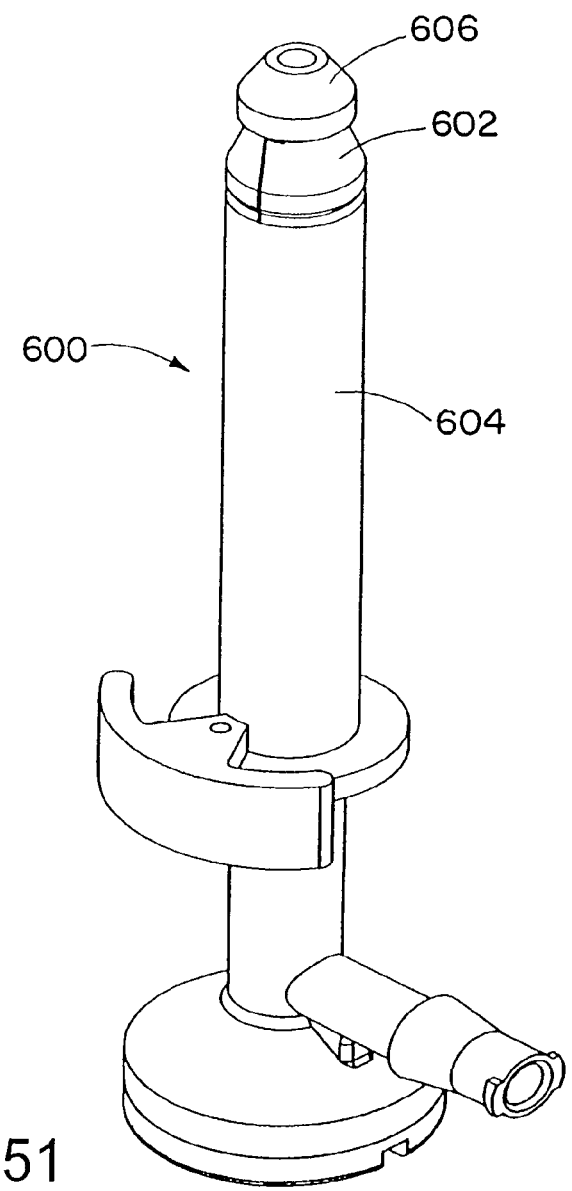
FIG. 51 is a perspective view of still another embodiment of a cannula system provided in accordance with the present invention.
Figure 52:
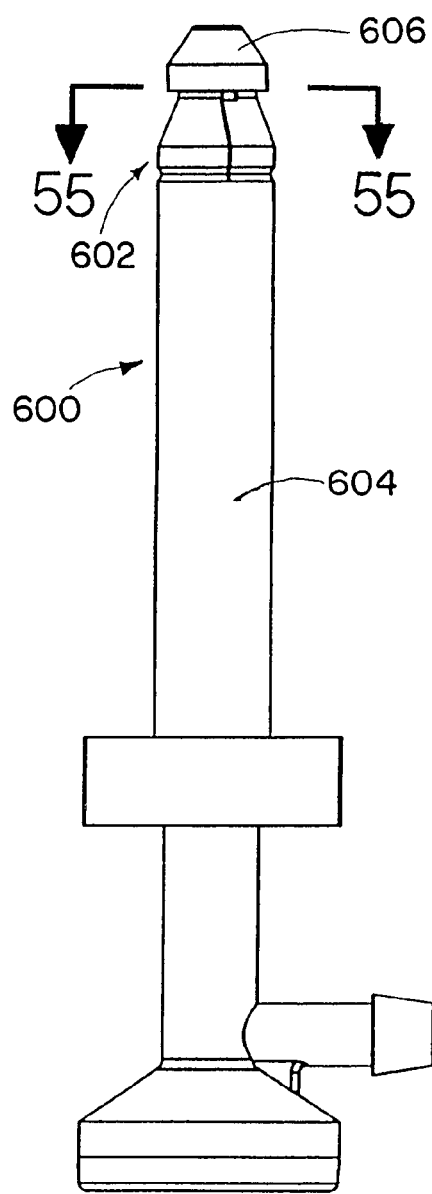
FIG. 52 is a side view of the cannula system of FIG. 51.
Figure 53:
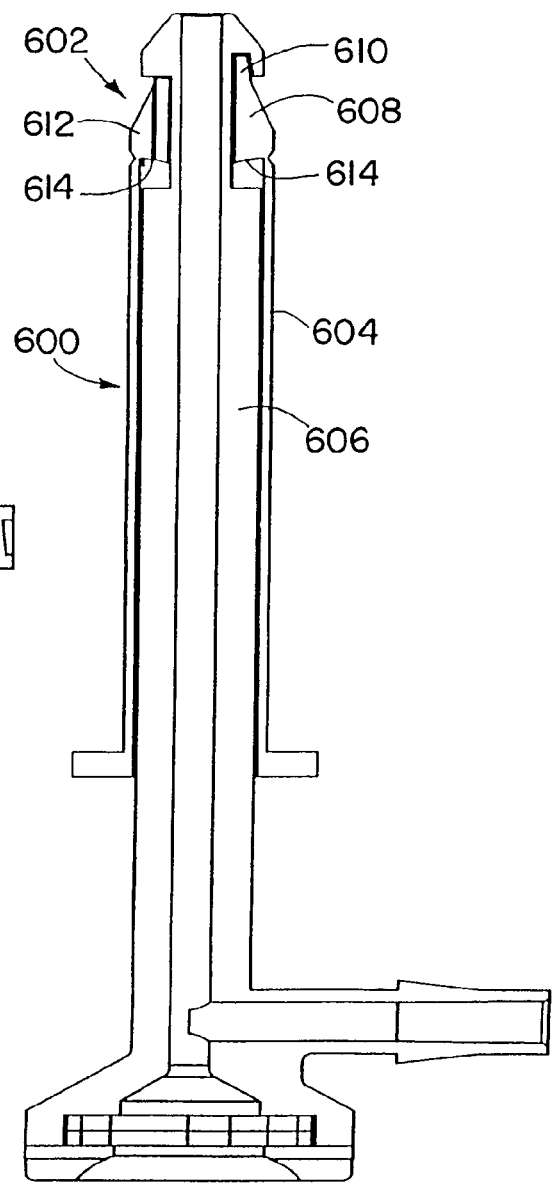
FIG. 53 is a cross-sectional view of the cannula system of FIG. 51.
Figure 54:
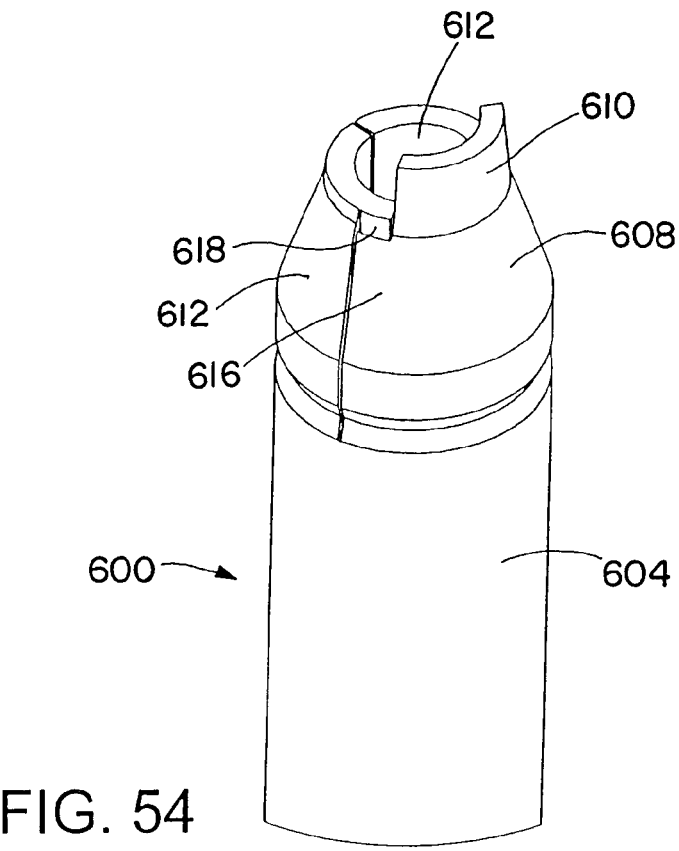
FIG. 54 is an enlarged view of a distal region of the cannula system of 51.
Figure 55:
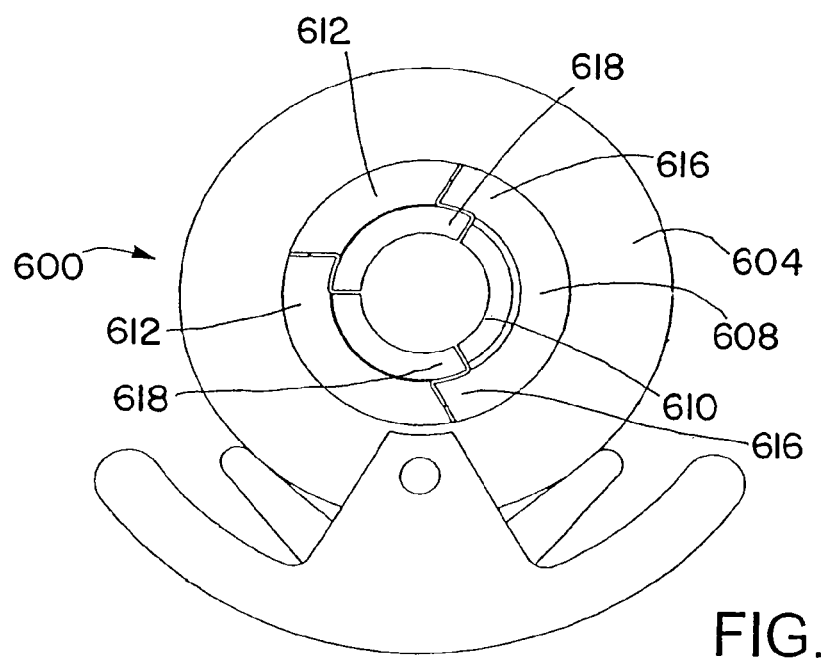
FIG. 55 is a cross-sectional view of the cannula system of 52 as seen along lines 55-55 of FIG. 52.

With the arm or arms 552 in the open position, the inner member 556 can be rotated so that the one or more recesses 562 no longer align with the one or more arms 552. To facilitate this, the inner member 556 may include indicia in a proximal region that indicates the angular placement of the one or more recesses 562. Now the arm or arms 552 cannot move into the recess or recesses 562 without rotating the inner member 556. The one or more ribs 564 hold the one or more arms 552 in the open position. Consequently, the inner member 556 can be retracted in the proximal direction from a distally extended position without releasing the one or more arms 552 from the open position, as shown in FIGS. 48-50. The ribs 564 also allow the inner member 556 to be withdrawn in a proximal direction, and even removed from the outer cannula 554, to release the arm or arms 552 from the open position before withdrawing the cannula system 550 from the patient's body.

In the embodiment shown in FIGS. 51 through 55, yet another cannula system 600 is shown. The cannula system 600 has a plurality of arms 602 connected to a distal end of an outer cannula 604 and an inner member 606 telescopically received in the outer cannula 604. The illustrated inner member 606 is a combined trocar and inner cannula as shown in the previous embodiment. In this system 600 one or more first arms 608 have a tab portion 610 at a distal end that is engaged by the inner member 606 to hold the first arm or arms 608 in the closed position. At least one second arm 612 is held in a closed position by elements that connect the first and second arms 608 and 612 together.

Advancing the inner member 606 disengages the tab portion 610 of the first arm or arms 608, releasing them to move to the open position. In this embodiment, advancing the inner member 606 not only deploys the first arm or arms 608 from the closed position, but also disengages the second arm or arms 612 from the first arm or arms 608 and deploys the second arm or arms toward the open position as the inner member 606 engages proximally-facing cam surfaces 614 of the first and second arms 608 and 612. In the illustrated embodiment, the elements that hold the second arm or arms 612 to the first arm or arms 608 include portions 616 of the first arm or arms 608 that overlap corresponding portions 618 of the second arm or arms 612. In the illustrated embodiment, the portions 616 of the first arm 608 are radially outward and circumferentially interlock the corresponding portions 618 of the second arms 612, preventing the second arms 612 from rotating outward until the first arm 608 is released from the inner member 606.

Yet another cannula system 700 provided by the present invention is shown in FIGS. 59-69. The cannula system 700 is similar to the cannula system 50 shown in FIG. 1, except as noted in the following paragraphs. As in the cannula system 50 of FIG. 1, the cannula system 700 shown in FIG. 59 includes a cannula assembly comprising an outer cannula 702 and an inner cannula 704 telescopically received within the outer cannula. The outer cannula 702 includes at least two arms 706 at its distal end that can be deployed to secure the cannula system 700 in place. The inner cannula 704 includes a transverse passage 710 (FIG. 68) near its proximal end for the introduction and removal of fluid. And a trocar 712 is telescopically received within the inner cannula 704 to facilitate placement of the cannula system 700 in the patient. The trocar 712 functions as an inner member to temporarily hold the arms 706 of the outer cannula 702 in their closed position for insertion of the cannula system 700 into the patient.

Turning to FIGS. 60-63, the outer cannula 702 includes a locking mechanism 720 to control the position of the outer cannula 702 relative to the inner cannula 704. The cannula locking mechanism 720 includes a catch 722 that is biased to bear against the outer surface of the inner cannula 704 and a corresponding detent 724 formed in the inner cannula's outer surface. In this case the detent is formed as an area with a reduced diameter, longitudinally adjacent one or more larger-diameter portions of the inner cannula 704. The reduced-diameter areas also form circumferential grooves so that rotational position is not important. Consequently, when the catch 722 engages a reduced-diameter area 724 the larger diameter portions generally limits the range of relative motion in a longitudinal direction between the inner cannula 704 and the outer cannula 702.

More particularly, the catch 722 of the locking mechanism 720 has a button portion 726 that protrudes from the outer cannula 702 and a central opening 728 for receipt of the inner cannula 704. Opposite the button 726 is a biasing mechanism that biases the button to an extended or locked position. In the illustrated embodiment, this biasing mechanism takes the form of a pair of integrally-formed inwardly-turning fingers 730. The fingers 730 are captured in a cavity in the outer cannula 702 opposite the button 726, on the other side of the passage that receives of the inner cannula 704. The fingers 730 act as springs. As the button 726 is pressed inwardly, the distal ends of the fingers 730 are pressed toward one another and the bearing surface of the catch 722 moves away from and out of the path of the inner cannula, generally releasing the inner cannula 704 to move relative to the outer cannula 702. In particular, pressing the button 726 moves the bearing surface of the catch 722 out of the detent 724 and allows the larger diameter portions to pass the catch 722. When the button 726 is released, the fingers 730 bias the button outward, to urge the bearing surface of the catch 722 against the outer surface of the inner cannula 704 and interfering with the larger-diameter portions so that the inner cannula 704 cannot be withdrawn from the outer cannula 702 without depressing the button 726. Depending on the force applied by the bearing surface, when the button 726 is not depressed the inner cannula 704 may move longitudinally relative to the outer cannula 702, but that longitudinal motion is limited by the distance the bearing surface of the catch 722 can move within the detent 724.

The distal side of one of the larger-diameter portions 732 is ramped, providing a gradually increasing diameter from the smaller diameter area to the larger diameter portion. The ramp allows the inner cannula 704 to be advanced in the proximal direction relative to the outer cannula 702 without depressing the button 726. To retract the inner cannula 704, however, the button 726 must be depressed to move the bearing surface of the catch 722 over a larger-diameter portion 732 of the inner cannula 704. Since the longitudinally-extended inner cannula 704 keeps the arms 706 in their extended open position, this prevents the arms 706 from inadvertently retracting toward the closed position. This type of locking mechanism is not restricted to the illustrated embodiment but may be employed in other embodiments. Moreover, a different type of locking mechanism that restricts unintended movement of the inner cannula 704 relative to the outer cannula 702 can be used in place of the locking mechanism in the illustrated cannula system 700.

Figure 64:
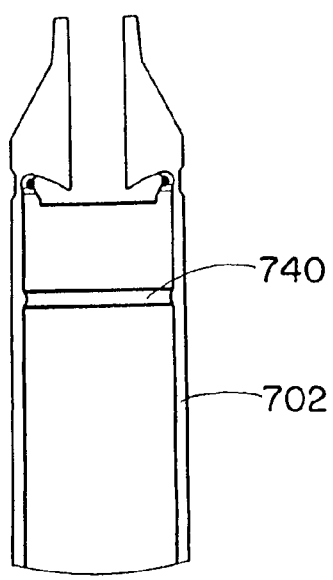
FIG. 64 is an enlarged cross-sectional view of the outer cannula portion of the cannula system of FIG. 59.

The cannula system 700 may further include at least one ring seal 740 between the inner cannula 704 and the outer cannula 702, shown in FIG. 64. The ring seal 740 is integrally formed in the inner surface of the outer cannula 702, and has a diameter that provides an interference fit with the outer diameter of the inner cannula 704. The outer cannula 702 is made of a plastic that can deform as the inner cannula 704 is telescopically inserted past the ring seal 740, thereby providing a sufficient seal to retain fluid in the surgical site. Alternately, the seal ring could be put on the outer diameter of the inner cannula.

Referring now to FIGS. 65-68, while the locking mechanism 720 prevents or minimizes unintentional retraction of the inner cannula 704 relative to the outer cannula 702, it is the trocar 712 that holds the system 700 together for insertion into the patient. At its proximal end, the trocar 712 includes an enlarged-diameter handle or handle portion 750. As in other embodiments, over most of its length the diameter of the trocar 712 generally is less than the inner diameter of the inner cannula 704 to minimize friction with the inner surfaces of the inner cannula 704 and its seals.

Toward its distal end the trocar 712 has a diameter that approaches the inner diameter of the inner cannula 704, however. This enlarged distal portion, referred to as the head or tip 752 of the trocar, has a cone-shape distal end 754, a relieved portion 756 proximally adjacent the base of the cone 754, and a ramped portion 758 with a distally increasing diameter proximally adjacent the relieved portion 756. The ramped portion 758 gradually increases in diameter toward its distal end to facilitate withdrawing the trocar 712 from the inner cannula 704 and through the seals at the proximal end of the inner cannula 704. The relieved portion 756 includes one or more recessed areas 760 that have a reduced diameter and a length and a width sufficient to receive the arms 706 in their closed position. Circumferentially adjacent the recessed areas 760, the trocar has a larger diameter area or rib 762, which reinforces the trocar 712 in the vicinity of the recessed areas 760 and can facilitate removing the trocar 712 from the inner cannula 704. The proximal side of the cone-shape distal end portion 754 is axially undercut or recessed to receive the distal ends of the arms 706 and hold them in their closed position while the cannula system 700 is inserted into the patient, similar to the previously-described embodiment shown in FIGS. 11-13. The arms are thus captured between the trocar 712 and the distal end of the inner cannula 704.

To minimize the opportunity for the trocar 712 to permanently deform the seals in the inner cannula 704, the trocar 712 typically is inserted just before the procedure. To assemble the cannula system 700, the trocar 712 is inserted through the inner cannula 704 until the proximal side of the cone 754 is past the distal end of the arms 706 connected to the outer cannula 702. The arms 706 are moved to and/or held in their closed position within the recessed areas 760, and the trocar 712 is retracted relative to the outer cannula 702 to capture the distal ends of the arms 706 in the recesses in the proximal side of the cone-shape distal end 754 of the trocar 712. Once the cannula system 700 is assembled, the outer cannula 702 defines a sleeve that surrounds the inner cannula 704, and the inner cannula 704 has a central passage for receipt of the trocar 712. Once assembled, the longer trocar 712 defines both the proximal and distal ends of the cannula system 700.

To lock the trocar 716 in position and keep the arms 706 from escaping until after the cannula system 700 is properly positioned in the patient, the trocar 712 includes a locking arm 770 as a locking device. The locking arm 770 is connected to the handle 750 by a pivot 772 toward a distal side of the handle 750. The locking arm 770 includes a grip portion 774 that the user can grasp and manipulate and a cam 776 opposite the grip 774 on the other side of the pivot 772. The locking arm 770 is movable between a locked position and a rotatably-displaced unlocked position. The grip 774 has a length dimension and in the locked position the grip 774 lies adjacent the handle 750 with its length dimension generally parallel to the longitudinal axis of the trocar 712. To keep the locking arm 770 in its locked position, the grip 774 engages a recess in the handle with a snap fit.

Figure 65:
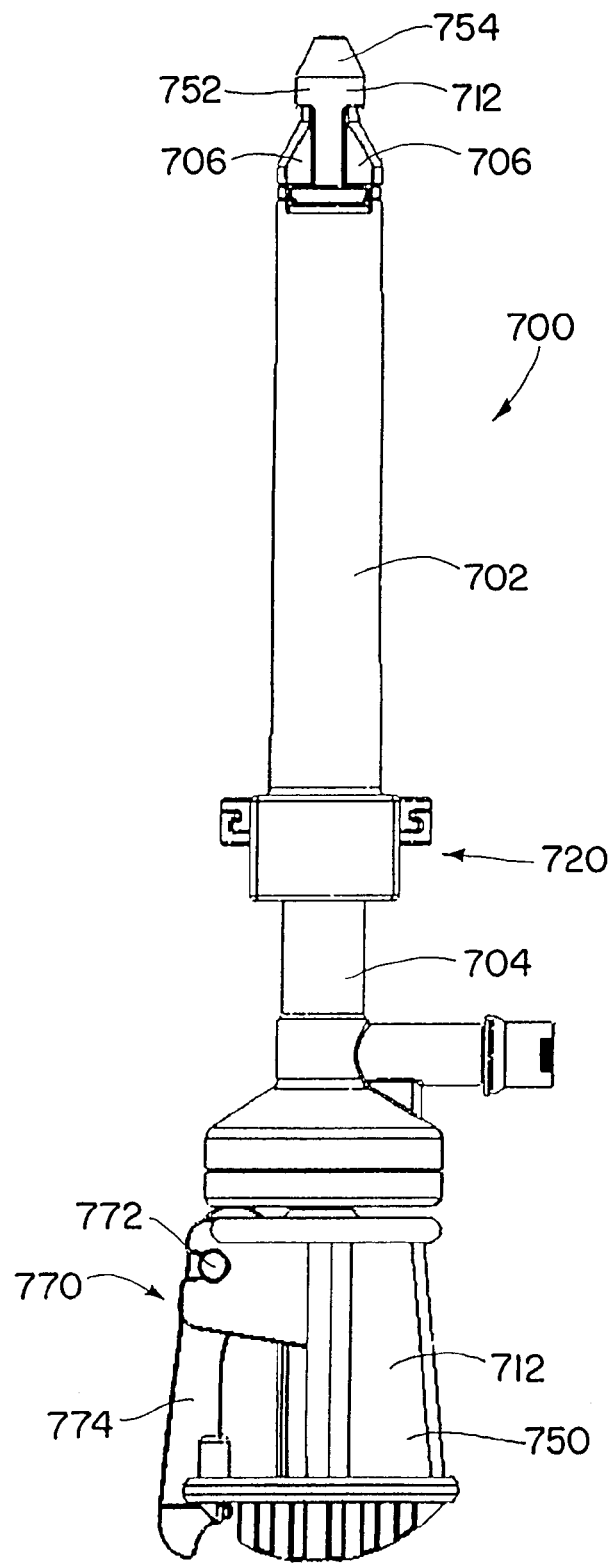
FIG. 65 is a side elevation view of the cannula system of FIG. 59 looking in the direction 65-65 shown in FIG. 59.

With the locking arm 770 in the locked position, the cam portion 776 protrudes beyond the distal end of the handle 750 to engage a proximal end of the inner cannula 704 (best shown in FIG. 65). With the locking arm 770 in its locked position the cam portion 776 defines a gap between the proximal side of the inner cannula 704 and the distal portion of the handle 750, retaining the arms 706 of the outer cannula 702 in their closed position, captured in the trocar 712. The outer cannula 702 in turn is prevented from moving relative to the inner cannula 704 by the trocar 712, which holds the arms 706 in the relieved portion 756 between the cone-shape tip 754 and the proximal shoulder of the relieved portion 756. More particularly, the outer cannula 702 is prevented from moving longitudinally by the inner-to-outer cannula lock provided via locking arm 770 and the cam portion 776 and from rotating by the undercut trocar tip 754 capturing the arms 706.

Figure 66:
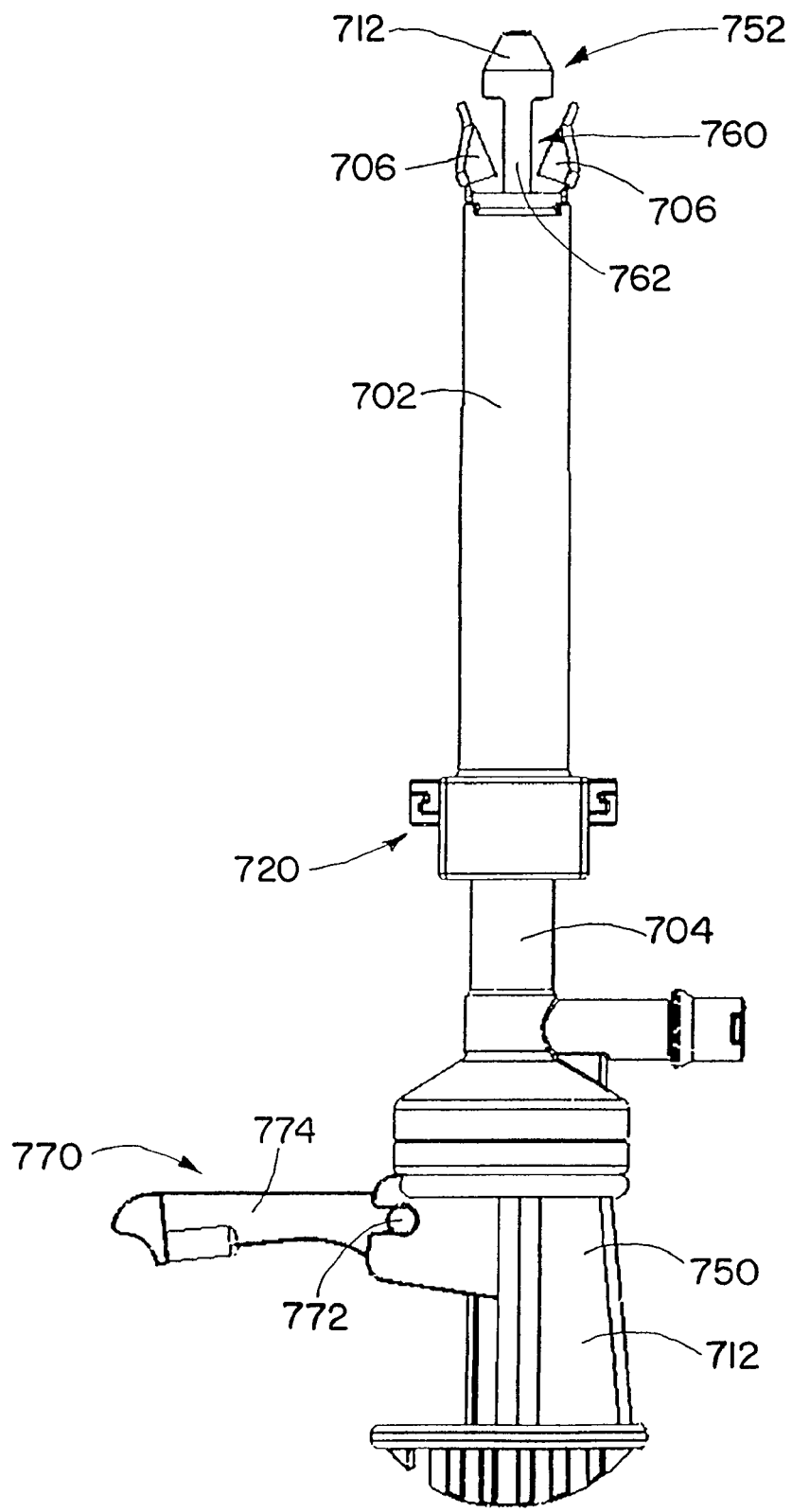
FIG. 66 is a side elevation view of the cannula system of FIG. 59 with wing portions released from the trocar.
Figures 67, 68:
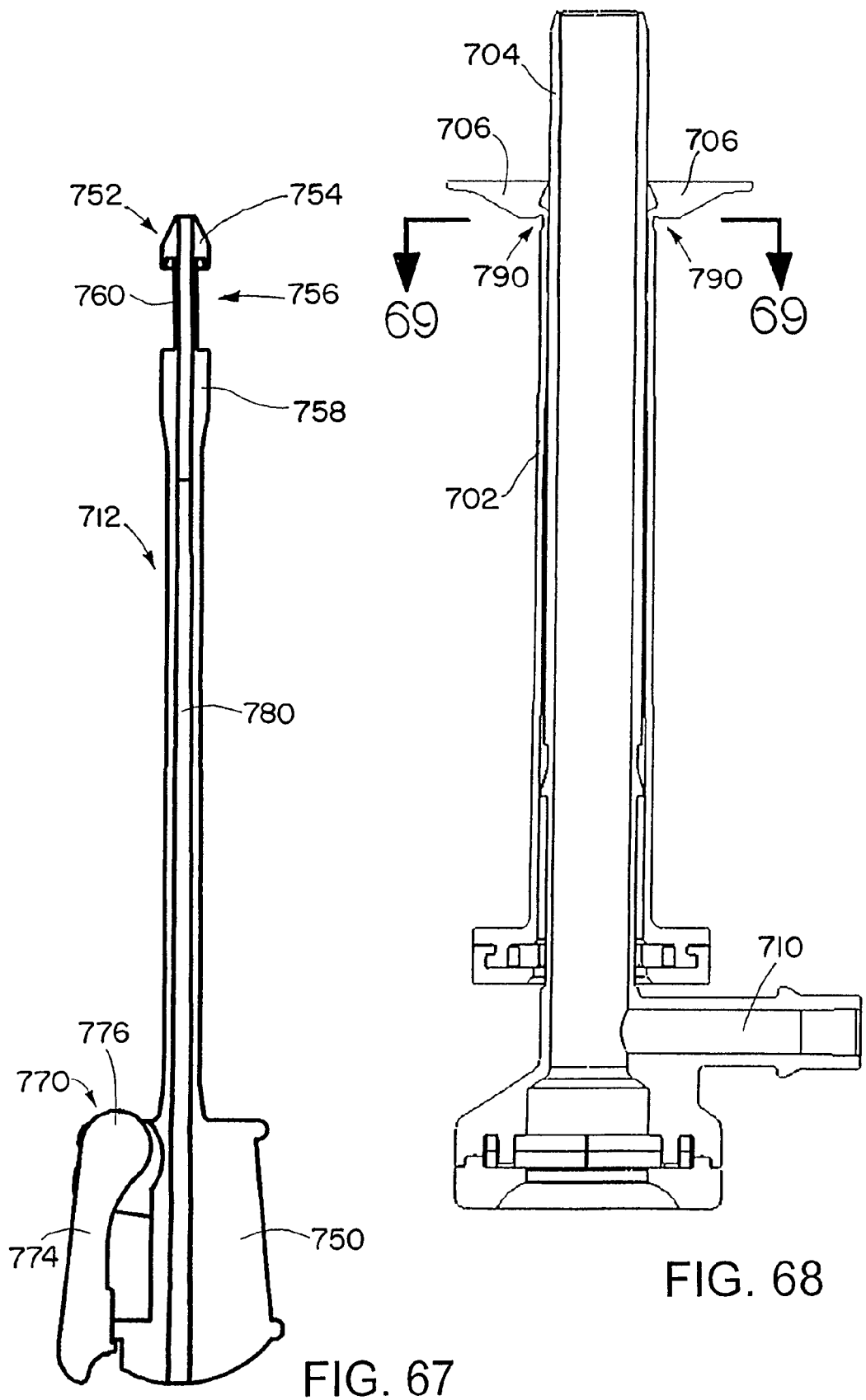
FIG. 67 is a cross-sectional side elevation view of a trocar portion of the cannula system of FIG. 59, looking in direction 65-65 at section 67-67 shown in FIG. 59.
FIG. 68 is a cross-sectional side elevation view of the cannula system of FIG. 59 with the trocar removed and the wings deployed.

When the locking arm 770 is moved to the unlocked position, and the grip 774 is swung up and away from the handle 750 as shown in FIG. 66, the cam portion 776 rotates into a recess in the handle 750, inward of the pivot 772. This allows the gap between the distal end of the handle 750 and the proximal end of the inner cannula 704 to close, releasing the arms 706 and allowing relative motion between the trocar 712 and the inner cannula 704. Advancing the trocar 712 relative to the inner cannula 704 closes that gap and frees the distal ends of the arms 706.

Typically, the surgeon advances the inner cannula 704 relative to the outer cannula 702 and deploys the arms 706 prior to withdrawing the trocar 712. At that point, removing the trocar 712 is a simple matter of pulling it out of the inner cannula 704. This secures the cannula assembly in position and minimizes the potential for dislodging the cannula assembly when the trocar 712 is removed. Alternatively, the surgeon can rotate the trocar 712 and remove it prior to deploying the arms 706. Rotating the trocar 712 brings the increased-diameter rib portions 762 adjacent the relieved areas 760 at the tip of the trocar 712 into engagement with the arms 706, which can ensure that the arms 706 are pushed out of the way and will not catch on the trocar 712 as it is withdrawn. Once the trocar 712 is removed, the inner cannula 704 can be advanced relative to the outer cannula 702 to deploy the arms 706 to the open position shown in FIG. 68.

To insert the cannula system 700, typically a cut is made through the layers of tissue to reach a surgical site in a body cavity. As in the other embodiments, the trocar 712 in this system has a central passage 780 for receipt of a guide wire or switching stick to help guide the cannula system to the surgical site. The tapered distal end of the cannula system 700 helps to push aside the tissue adjacent the cut as the cannula system 700 enters the body. After insertion, the locking arm 770 is released by pivoting the grip 774 away from the handle portion 750 of the trocar 712 to withdraw the cam 776 into its recess and the trocar 712 is advanced to move the proximal side of the cone 754 past the distal ends of the arms 706. Then the inner cannula 704 can be advanced relative to the outer cannula 702 to deploy the arms 706. The arms 706 may move outward automatically, or the trocar 712 can be rotated to push the arms 706 outward using the larger-diameter ribs 762 adjacent the relieved areas 760. Then the trocar 712 can be withdrawn through the inner cannula 704 without catching on the arms 706.

Once the arms 706 have been released from the trocar 712, the inner cannula 704 can be advanced within the outer cannula 702 to engage a cam surface on a proximal side of the arms 706 and push them outward. Advancing the inner cannula 704 past the arms 706 locks the arms 706 in the open position. As the inner cannula 704 advances, the catch 722 (FIG. 61) of the cannula locking mechanism 720 advances past the ramped enlarged diameter portion 732 on in the outer surface of the inner cannula 704, which keeps the distal end of the inner cannula 704 extended past the arms 706 so that they do not inadvertently retract toward their closed position. After deploying the one or more arms 706 to the open position, the inner cannula 704 may be further advanced beyond the distal end of the outer cannula 702.

To withdraw the cannula system 700, the button 726 (FIG. 61) on the cannula locking mechanism 720 is pushed inwardly, withdrawing the bearing surface of the catch 722 and allowing the inner cannula 704 to be retracted past the arms 706. In fact, the inner cannula 704 can be withdrawn completely from the outer cannula 702. Without the inner cannula 704 adjacent the arms 706, there is nothing to hold the arms 706 open and the outer cannula 702 can be withdrawn from the patient.

Figure 69:
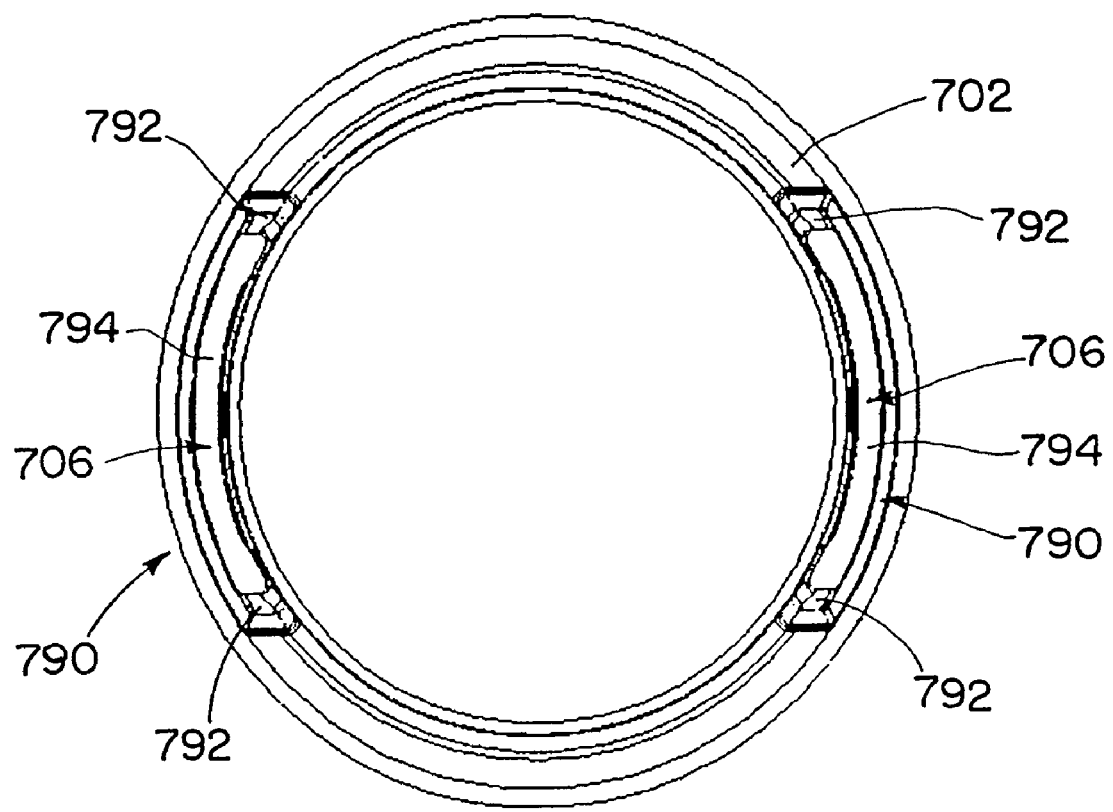
FIG. 69 is a transverse cross-sectional view of the outer cannula of FIG. 59.

Finally, in the illustrated embodiment each arm 706 is integrally connected to the distal region of the outer cannula 702 with a living hinge 790. As shown in FIG. 69, the hinge 790 is relatively thicker at circumferentially opposite sides of the arm 706 to define reinforcing ribs 792 on opposite sides of a reduced thickness hinge section 794. This structure reinforces each arm 706 without significantly impairing the bendability of the material that forms the hinge.

The devices, systems and methods described herein are particularly useful for endoscopic surgery, but may have application to other types of minimally invasive surgery, including "mini-open" procedures.

Although the invention has been shown and described with respect to certain embodiments, equivalent alterations and modifications will occur to others skilled in the art upon reading and understanding this specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function of the described integer (i.e., that is functionally equivalent), even though not structurally equivalent to the disclosed structure which performs the function in the herein illustrated exemplary embodiments of the invention.

What is claimed is:

1. A cannula system, comprising: an outer cannula; at least one arm that is deployable between a closed position and an open position and is connected to the outer cannula toward a proximal end of the at least one arm; an inner member telescopically received in the outer cannula that engages at least one arm and holds it in the closed position; the inner member being deployable to disengage the inner member from the at least one held arm; and another inner member engaging and moving each arm from the closed position to the open position upon deployment of the other inner member.

2. A system as set forth in claim 1, wherein the inner member has an enlarged tip portion at a distal region thereof, and an element of the tip portion holds the at least one held arm in the closed position.

3. A system as set forth in claim 2, wherein the element of the inner member tip portion includes a recess and the at least one held arm has a tab portion that is receivable in the recess to prevent the arm from deploying from the closed position.

4. A system as set forth in claim 2, wherein the element that holds the at least one arm in the closed position includes a groove.

5. A system as set forth in claim 1, wherein each arm rotates about a respective pivot axis at a proximal end of the arm near where the arm is connected to the outer cannula.

6. A system as set forth in claim 1, comprising a plurality of arms, at least one first arm having a first element that engages the at least one first arm to the inner member, and at least one second arm having a second element that engages the at least one second arm to the at least one first arm when the at least one first arm is in the closed position.

7. A system as set forth in claim 1, wherein the inner member includes a trocar that engages the at least one arm and holds it in the closed position.

8. A system as set forth in claim 7, wherein the other inner member includes an inner cannula telescopically received in the outer cannula, and the trocar is telescopically received in the inner cannula; and the trocar includes a locking device; and wherein when the trocar is holding the at least one arm in the closed position the at least one arm is captured between the trocar and a portion of the inner cannula, and when the locking device is engaged the trocar is held in a fixed location relative to a longitudinal axis of the inner cannula.

9. A system as set forth in claim 1, wherein the other inner member includes an inner cannula telescopically received in the outer cannula.

10. A system as set forth in claim 9, wherein when a distal end of the inner cannula is advanced to longitudinally extend beyond its point of contact with the at least one arm the inner cannula holds the at least one arm in the open position.

11. A system as set forth in claim 1, wherein each arm is integrally connected to the outer cannula with a living hinge, and each arm is pivotable about a point within a cylinder with infinite length and a diameter defined by an outer surface of the outer cannula, whereby each arm is outwardly rotatable about the pivot point between the closed position and the open position.

12. A system as set forth in claim 11, wherein the living hinge has a reduced material thickness in an inner portion and relatively thicker lateral portions on opposing sides of the inner portion.

13. A system as set forth in claim 1, wherein at least one arm has a cam surface that extends inside the outer cannula for engagement by the other inner member to move each arm from the closed position.

14. A system as set forth in claim 1, wherein the other inner member includes an inner cannula telescopically received in the outer cannula, and a catch mechanism that releasably limits longitudinal travel of the inner cannula relative to the outer cannula when the at least one arm has moved from the closed position.

15. A system as set forth in claim 1, wherein the other inner member includes an inner cannula, and advancing the inner cannula past the proximal end of the at least one arm moves the at least one arm to the open position and holds it there until the inner cannula is withdrawn from contact with the at least one arm.

16. A cannula system as set forth in claim 1 wherein the at least one arm extends generally parallel to a longitudinal axis of the outer cannula when in the closed position and extends transverse to the longitudinal axis of the outer cannula when in the open position.

17. A cannula system as set forth in claim 16 wherein the other inner member moves in a distal direction relative to the outer cannula to move the at least one arm from the closed position to the open position.

18. A cannula system as set forth in claim 16 wherein the other inner member is telescopically received in the outer cannula and the inner member is telescopically received in the other inner member, the inner member engages the at least one arm to hold the at least one arm in the closed position.

19. A cannula system as set forth in claim 18 wherein the other inner member engages the at least one arm to hold the at least one arm in the open position.

20. A cannula system as set forth in claim 19 wherein the inner member includes a locking mechanism that prevents relative movement between the inner member and the other inner member when the at least one arm is in the closed position.

21. A cannula system as set forth in claim 19 wherein the inner member moves in a distal direction relative to the outer cannula to release the at least one arm for movement from the closed position to the open position.

22. A cannula system as set forth in claim 19 wherein the inner member moves in a proximal direction relative to the outer cannula to release the at least one arm for movement from the closed position to the open position.

23. A cannula system as set forth in claim 18 wherein the other inner member moves in a distal direction relative to the outer cannula and engages the at least one arm to move the at least one arm from the closed position to the open position.

24. A cannula system as set forth in claim 16 wherein the other inner member includes a radially outer surface that engages the at least one arm when the at least one arm is in the open position to hold the at least one arm in the open position.

25. A method of using a cannula system for introducing a medical instrument into a patient, comprising the steps of
(A) inserting a cannula system into the body of a patient, the cannula system having an outer cannula and an inner member telescopically received in the outer cannula, the outer cannula having at least one arm attached thereto by a connection toward a proximal end of the at least one arm, and the at least one arm is held in a closed position by the inner member;
(B) deploying the inner member to disengage the at least one arm from the inner member and allow the at least one arm to deploy to an open position displaced from the closed position; and
(C) moving another inner member to deploy each arm from the closed position to the open position and move each arm from the closed position to the open position, the inner member engaging and moving each arm from the closed position to the open position.

26. A method as set forth in claim 25, comprising the step of securing the inner member in a fixed location relative to a longitudinal axis of the outer cannula with the at least one arm in the closed position.

27. A method as set forth in claim 25, wherein the moving step includes longitudinally advancing the other inner member to engage the at least one arm and move the at least one arm to the open position, the other inner member holding the at least one arm in the open position when the inner member is in a longitudinally-extended position.

28. A method as set forth in claim 27, wherein the other inner member includes an inner cannula telescopically received in the outer cannula and the inner member includes a trocar telescopically received in the inner cannula, and the deploying step includes advancing the trocar to disengage the at least one arm, and then advancing the inner cannula relative to the outer cannula to deploy the arms to the open position.

29. A method as set forth in claim 28, wherein corresponding elements of the inner cannula and the outer cannula cooperate to limit longitudinal travel of the inner cannula when the inner cannula has advanced to deploy the at least one arm to the open position.

30. A method as set forth in claim 27, comprising the step of retracting the other inner member to release the at least one arm from the open position.

* * * * *